(12) United States Patent
Deming et al.

(10) Patent No.: US 8,691,204 B2
(45) Date of Patent: Apr. 8, 2014

(54) SYNTHETIC DIBLOCK COPOLYPEPTIDE HYDROGELS FOR USE IN THE CENTRAL NERVOUS SYSTEM

(75) Inventors: Timothy J. Deming, Los Angeles, CA (US); Michael V. Sofroniew, Los Angeles, CA (US); Chu-Ya Yang, Changhua (TW); BingBing Song, Los Angeles, CA (US); Yan Ao, Harbor City, CA (US)

(73) Assignee: The Regents of the University of California, Oakland, CA (US)

( * ) Notice: Subject to any disclaimer, the term of this patent is extended or adjusted under 35 U.S.C. 154(b) by 293 days.

(21) Appl. No.: 13/201,974

(22) PCT Filed: Feb. 18, 2010

(86) PCT No.: PCT/US2010/024603
§ 371 (c)(1),
(2), (4) Date: Aug. 17, 2011

(87) PCT Pub. No.: WO2010/096572
PCT Pub. Date: Aug. 26, 2010

(65) Prior Publication Data
US 2012/0093722 A1    Apr. 19, 2012

Related U.S. Application Data

(60) Provisional application No. 61/153,527, filed on Feb. 18, 2009, provisional application No. 61/186,671, filed on Jun. 12, 2009.

(51) Int. Cl.
*A61K 31/74*    (2006.01)
(52) U.S. Cl.
USPC .................................... 424/78.17; 424/78.08
(58) Field of Classification Search
None
See application file for complete search history.

(56) References Cited

U.S. PATENT DOCUMENTS

| | | |
|---|---|---|
| 6,686,446 B2 | 2/2004 | Deming et al. |
| 2002/0032309 A1 | 3/2002 | Deming et al. |
| 2003/0147958 A1 | 8/2003 | Ahn et al. |
| 2005/0031522 A1 | 2/2005 | Delaney et al. |
| 2008/0125581 A1 | 5/2008 | Deming et al. |

FOREIGN PATENT DOCUMENTS

| | | |
|---|---|---|
| WO | WO-01/94379 A2 | 12/2001 |
| WO | WO-2006/113667 A1 | 10/2006 |
| WO | WO-2008/070571 A2 | 6/2008 |

OTHER PUBLICATIONS

Tian et al. "Hyaluronic acid-poly-D-lysine-based three-dimensional hydrogel for traumatic brain injury", Tissue Eng Mar.-Apr. 2005, vol. 11, No. 3-4, pp. 513-525.

Hou et al., "The repair of brian lesion by implantation of hyaluronic acid hydrogels modified with laminin", J. Neurosci Meth Oct. 2005, vol. 148, No. 1, pp. 60-70.

Lin et al. "Chondroitinase ABC has a long-lasting effect on chondroitin sulphate glycosaminoglycan contenet in the injured rat brain", J. Neurochem, Jan. 2008, vol. 104, No. 2, pp. 400-408. (Abstract only).

Nowak, et al., Rapidly recovering hydrogels scaffolds from self-assembling diblock copolypeptide amphiphiles. Nature May 23, 2002, vol. 417, No. 6887, pp. 424-428.

Dondoni et al., "The emergence of thiol-ene coupling as a click process for materials and bioorganic chemistry". Angew Cehm Int Ed Engl. 2008, vol. 47, No. 47, pp. 8995-8997.

International Search Report issued in PCT/US2010/24603, dated Sep. 28, 2010.

Japanese Office Action dated Nov. 27, 2012, issued in Japanese Patent Application No. 2009-539522.

Bermudez et al. "Molecular Weight Dependence of Polymersome Membrane Structure, Elasticity, and Stability," Macromolecules 35:8203-8208 (2002).

Brooks, et al. "Tat peptide-mediated cellular delivery: back to basics," Adv. Drug Deliv. Rev. 57:559-577 (2005).

Calnan et al. "Arginine-mediated RNA recognition: the arginine fork," Science 252:1167-1171 (1991).

Deming, T. J. "Cobalt and iron initiators for the controlled polymerization of alpha-amino acid-N-carboxyhanhydrides," Macromolecules 32:4500-4502 (1999).

Deming, T.J. "Facile synthesis of block copolypeptides of defined architecture," Nature 390:386-389 (1997).

Discher, et al. "Polymer vesicles in various media," Curr. Opn. Coll. Interface. Sci. 5:125-145 (2000).

Futaki, S. "Membrane-permeable arginine-rich peptides and the translocation mechanisms," Adv. Drug Deliv. Rev. 57:547-558 (2005).

Holowka et al. "Charged Polypeptide Vesicles with Controllable Diameter," J. Amer. Chem. Soc. 127:12423-12428 (2005).

Kim et al. "Pharmacodynamics of insulin in polyethylene glycol-coated liposomes," Int. J. Pharm., 180:75-81 (1999).

Mitchell et al. "Polyarginine enters cells more efficiently than other polycationic homopolymers," J. Peptide Res. 56:318-325 (2000).

Mosmann, T. "Rapid colorimetric assay for cellular growth and survival: Application to proliferation and cytotoxicity assays," Journal of Immunological Methods 65:55-63 (1983).

Pakstis et al. "The Effect of Chemistry and Morphology on the Biofunctionality of Self-Assembling Diblock Copolypeptide Hydrogels," Biomacromolecules 5:312-318 (2004).

(Continued)

*Primary Examiner* — James Rogers
(74) *Attorney, Agent, or Firm* — Venable LLP; Nancy J. Axelrod; Henry J. Daley

(57) ABSTRACT

This invention relates, e.g., to a composition suitable for administration to the central nervous system (CNS), comprising a block copolypeptide hydrogel, which comprises a biologically active material that is mixed with the hydrogel or that is attached to the polypeptide chain of the hydrogel, wherein the composition is suitable for administration to the CNS. Also disclosed are methods of making and using compositions of the invention as depots or as scaffolds for cell migration, and pharmaceutical compositions and kits for implementing methods of the invention.

16 Claims, 16 Drawing Sheets

(56) References Cited

OTHER PUBLICATIONS

Proctor, J. "Blood Substitutes and Experimental Models of Trauma," Trauma, 54, S106 (2003).
Rabinovici et al. "Liposome-Encapsulated Hemoglobin: An Oxygen-Carrying Fluid," Circulatory Shock, 32:1 (1990).
Riess, "Oxygen Carriers ("Blood Substitutes")—Raison d'Etre, Chemistry and Some Physiology" Chem. Rev., 101:2797 (2001).
Rothbard et al. "Adaptive translocation: the role of hydrogen bonding and membrane potential in the uptake of guanidinium-rich transporters into cells," Adv. Drug. Deliv. Rev. 57:495-504 (2005).
Rothbard et al. "Conjugation of arginine oligomers to cyclosporin A facilitates topical delivery and inhibition of inflammation," Nature Medicine 6:1253-1257 (2000).
Rothbard et al. "Role of membrane potential and hydrogen bonding in the mechanism of translocation of guanidinium-rich peptides into cells," J. Amer. Chem. Soc., 126:9506-9507 (2004).
Sakai et al. "Anion-mediated transfer of polyarginine across liquid and bilayer membranes," J. Amer. Chem. Soc., 125:14348-14356 (2003).
Sela et al. "Biological Properties of Poly Amino Acids," Adv. Protein Chem. 14:391-478 (1959).
Torchilin et al. "TAT peptide on the surace of liposomes affords their efficient intracellular delivery even at low temperature and in the presence of metabolic inhibitors," Proc. Natl. Acad. Sci. USA 98:9786-8791 (2001).
Tseng et al. "Translocation of liposomes into cancer cells by cell-penetrating peptides Peenetratin and Tat: a kinetic and efficacy study," Mol. Phamacol. 62:864-872 (2002).
Wadia et al. "Transducible TAT-HA fusogenic peptide enhances escape of TAT-fusion proteins after lipid raft macropinocytosis," Nature Medicine 10:310-315 (2004).
Wadia et al. "Transmembrane delivery of protein and peptide drugs by TAT-mediated transduction in the treatment of cancer," Adv. Drug Deliv. Rev. 57:579-596, 2005.
Indian Office Action, dated Feb. 22, 2013 issued in Application No. 1231/mumnp/2009.
Discher, et al. "Polymer Vesicles" *Science* 297, 967 (2002).
Yang et al., "Biocompatibility of amphiphilic diblock copolypeptide hydrogels in the central nervous system", Biomaterials, 2009, pp. 2881-2898, 30.
Supplementary European Search Report dated Nov. 9, 2012.

R—SH = thiolated protein

SYNTHETIC DIBLOCK COPOLYPEPTIDE HYDROGELS FOR USE IN THE CENTRAL NERVOUS SYSTEM

This application is a U.S. National Stage Application of Application No. PCT/US10/024603, filed Feb. 18, 2010 and claims the benefit of the filing dates of U.S. provisional application 61/,153,527, filed Feb. 18, 2009 and U.S. provisional application 61/186,671, filed Jun. 12, 2009, all of which are incorporated by reference herein in their entireties.

BACKGROUND INFORMATION

Many bioactive molecules with therapeutic potential for the central nervous system (CNS) exert wide-ranging activities that can lead to unwanted side effects if they are delivered systemically. A number of potential therapies for neurological conditions have failed in clinical trials for this reason. Site-specific delivery of potential therapies is increasingly recognized as an important goal for many neurological conditions, and biomaterial vehicles represent a promising means of achieving this goal. However, suitable vehicles are not presently available for the restricted targeting of growth factors or other diffusible molecules, or the placement of extracellular matrices for axon growth or cell migration. Furthermore, neural stem/progenitor cell grafts may hold promise for replacing lost cells in certain neurological conditions, but most current grafting procedures are regarded as resulting in suboptimal survival and differentiation of cells. Biomaterial vehicles may be able to improve grafting efficiency by providing grafted cells with support matrix and molecular substrates that help them overcome the shock of the grafting procedure and integrate and differentiate better in to host tissue.

Injectable biomaterials represent a rapidly advancing new area for delivery of therapeutic molecules. The U.S. F.D.A. has already approved certain biomaterials for slow release, long-term systemic drug delivery, while others are currently undergoing clinical trials The basic precedent of using biomaterials for drug delivery in humans has thus been set, but no materials are currently approved for delivery into the CNS.

Hydrogels are a class of materials that have significant promise for use in soft tissue and bone engineering (Lee et al. (2001) Hydrogels for tissue engineering, *Chemical Reviews* 101, 1869-1879). An important feature of hydrogels that makes them attractive for these applications is their well hydrated, porous structure that can mimic natural extracellular matricies (Peppas et al. (2000) Physicochemical foundations and structural design of hydrogels in medicine and biology, *Annual Review of Biomedical Engineering* 2, 9-29). To replace natural materials, however, many structural and functional features must be built into synthetic hydrogels. Desirable features include: biocompatability; degradability to allow cell ingrowth; injectable yet also fast setting in the wound site; mechanical properties that can be tuned for different uses; control over cell adhesion to the hydrogel matrix; and tunable sustained release of growth factors and other biologically active agents. There are many examples where some, or even most of these features have been incorporated into hydrogels. However, in many cases, hydrogel synthesis and formation becomes very complicated, which limits the practicality of such materials. More importantly, the complexity of these systems, combined with limited means for adjustment of molecular parameters, leads to the inability to independently adjust most of the features. For example, it would be advantageous to be able to adjust scaffold rigidity while maintaining a constant hydrogel mesh size. Such a system would allow one to directly measure the effects of scaffold rigidity on cell proliferation. Also, since hydrogel degradation is commonly accomplished using degradable crosslinkers (e.g. in PEG based hydrogels), it can be difficult to adjust degradation rate without also altering crosslink density, and hence initial gel mechanical properties. It would be desirable to have a hydrogel system where many of these desirable adjustable features (e.g. gel strength, gel density, adhesive capability, degradation rate, growth factor release rate) could be controlled independently so that, e.g., meaningful evaluations of their roles in tissue regeneration could be systematically evaluated. Currently, in many systems it is difficult to identify the most important gel characteristics, since many features are adjusted simultaneously.

Current hydrogel technology utilizes both naturally-derived macromolecules and synthetic polymers. Generally, hydrogels prepared from natural polymers possess desired biological signalling capability but may lack desired material properties, e.g. low sample rigidity, and may also be problematic due to immunogenicity and pathogen transmission issues. By contrast, synthetic polymers can be engineered for desired material properties but may display limited cytocompatibility. One approach to increase the cytocompatibility of synthetic polymers is to incorporate peptide epitopes, for example RGD motifs. However, incorporating these motifs into preformed polymers in a regiospecifically controlled manner is extremely difficult. In addition, these scaffolds are structurally homogeneous (not porous) on the microscale due to their underlying molecular network structure, which can limit cell proliferation. These systems must undergo additional processing (e.g. freeze-thaw cycling, particulate leaching, microsphere sintering and non-woven fiber formation) in order to introduce microscale porosity in the gel network. However, despite their dilute, porous nature, these well hydrated materials must also be mechanically rigid. This apparent contradiction, rigidity from a dilute porous scaffold, must be inherently addressed by the design of constituent molecular crosslinks (chemical and/or physical) formed during the hydrogelation process. However, introducing chemical crosslinks may be biologically problematic since by-products from the crosslinking chemistry may be toxic and difficult to remove from the scaffold. It would be desirable to generate benign, biocompatible chemical or physical crosslinking methods for either in vitro gelation for eventual incorporation in the body or direct, rapid in vivo gelation. An additional design complication is that hydrogel rigidity seemingly precludes any viable processability in preformed scaffolds. For example, one may wish to form a rigid tissue engineering construct in vitro but subsequently inject it into a host for tissue regeneration. Injection is not possible in a permanently crosslinked, rigid network. In short, the many seemingly contradictory features required in hydrogels for tissue engineering applications severely prohibits the use of materials with a large degree of adjustability in their properties. The polymers used in most synthetic hydrogels simply do not contain enough functionality to allow tuning of degradability, adhesion or gel strength without compromising other necessary properties.

Amphiphilic diblock copolypeptide hydrogels (referred to herein as "DCH") are synthetic materials with many features that make them attractive as tissue engineering candidates for applications that are likely to require progressive adjustment and fine-tuning of material properties (Pakstis et al. (2004) Effects of Chemistry and Morphology on the Bifunctionality of Self-Assembling Diblock Copolypeptide Hydrogels, *Biomacromolecules* 5, 312-318); Deming (2005) Polypeptide hydrogels via a unique assembly mechanism, *Soft Matter* 1, 28-39). The present inventors have previously used a combination of chemical synthesis and structural characterization to establish an understanding of DCH structure-property relationships that allows a high level of control over gel strength, gel porosity, gel functionality and media stability; and many of these properties can be adjusted independently of each other (Nowak et al. (2002) Rapidly recovering hydrogel scaffolds from self-assembling diblock copolypeptide amphiphiles, *Nature* 417, 424-428; Breedveld et al. (2004) Rheology of block copolypeptide solutions: hydrogels with tunable properties, *Macromolecules,* 3943-395)). DCH are physically associated gels that can be deformed and thinned by stress and injected through small-bore cannulae, after which they rapidly re-assemble into rigid gel networks (Nowak et al. (2002) (supra)). These properties provide DCH with the potential for facile and minimally invasive delivery in vivo. DCH form elastic gels with fibril-like nanostructures and porous microstructures theoretically suitable for integration with host cells (Nowak et al. (2002), (supra); Deming (2005), (supra).

It was unknown prior to the present invention whether DCH could be generated that are suitable for administration to the CNS, or whether such DCH could serve as depots for biologically active materials or act as scaffolds to support cell migration in the CNS.

DESCRIPTION OF THE DRAWINGS

FIG. 1A: Amphiphilic DCH are composed of variable-length chains of hydrophilic and hydrophobic amino acids. FIG. 1B: For this study, total chain length was kept constant at 200 amino acids on average, and the relative proportions of hydrophilic to hydrophobic components varied. The SEQ ID NOs for the polypeptides are, reading from left to right, SEQ ID NO:40, 7, 8, 9 and 10. FIG. 1C: In aqueous solutions, hydrophobic segments associate to form elongated fibrillar tape-like assemblies that branch and entangle to form 3D networks with hydrophilic segments exposed.

FIGS. 2A and 2B show schematic representations of the mouse brain (FIG. 2A) and of a frontal section (FIG. 2B) through the forebrain (dashed lines and dashed arrow) at the level of the caudate putamen nucleus (CPN), with solid arrows showing locations of injection sites of DCH deposits. FIG. 2C shows a survey photomicrograph of a cresyl violet stained tissue section showing a deposit (solid arrow) of the DCH, $K_{180}L_{20}$, in the CPN at 1 week after stereotaxic injection. Scale bar=500 µm. v=ventricle; cc=corpus callosum

FIGS. 4A and 4B show survey (FIG. 4A) and detail (FIG. 4B) light-microscopic images of 3% -$K_{180}L_{20}$ at 1 week after injection of 2 µl into the CPN and examined in semithin (0.3 µm) plastic sections stained with toluidine blue. Note the porous network structure of the DCH deposit, the thin layer of glial and inflammatory cells bordering the deposit, and the normal appearance of the immediately adjacent CPN tissue. FIGS. 4C-4H show electron microscopic images of ultrathin sections of the same tissue shown in FIG. 4B taken from regions approximately equivalent to the boxes indicated in FIG. 4B. FIG. 4C shows the porous network structure of the deposit composed of DCH fibrils (dch). FIG. 4D shows the interdigitation of glial and microglial cell processes into the border of the DCH forming a smooth and continuous transition from host to deposit. FIG. 4E shows at lower magnification the normal appearance of the CPN neuropil within 250 to 300 µm of the DCH deposit. FIGS. 4F-4G show at higher magnification details of normally appearing myelinated axons (FIG. 4F), normally appearing synapses with synaptic densities and pre-synaptic vesicles (arrows in FIGS. 4G and 4H), and various other normally appearing subcellular structures such as synaptic vesicles and mitochondria (FIGS. 4G and 4H). In FIGS. 4D-4G, note the absence of any detectable diffusion of DCH particles or fibrils through the extracellular space of the neuropil adjacent to the DCH deposit. Scale bars A=50 µm, B=25 µm, C=2.5 µm, D, E=1.5 µm, F-H=0.25 µm.

FIGS. 10A-10H show survey (FIGS. 10A, 10E) 3%-$K_{180}L_{20}$: no CSPGs were digested by chABC. Both sides of the forebrain in the WFA and 2B6 stained tissues show the same intensity of staining. (FIGS. 10B, 10F, 10I) 3%-$K_{180}L_{20}$ mixed with penicillinase: control groups to the chABC digestion on CSPGs. Both sides of the forebrain in the WFA and 2B6 stained tissues show the same intensity of staining. Detail image from box in FIG. 10F (FIG. 10I) shows the normal appearance and density of CSPGs in vivo. (FIG. 10C, FIG. 10G) chABC injected into the CPN of the left side in the forebrain. 2B6 stained tissue exhibited a darker color on the left side and lighter color on the left side in WFA stained tissue. (FIG. 10D, 10H, 10J) 3%-$K_{180}L_{20}$ mixed with chABC injected into the CPN of left side in the forebrain. 2B6 stained tissue exhibited a darker color on the left side and lighter color on the left side in WFA stained tissue. chABC retains its bioactivity and was released from DCH deposit over time. Detail image from box in FIG. 10H (FIG. 10J) shows the reduced density of CSPGs in vivo.

FIGS. 11A-11P show light-microscopic images of chABC at 1 (FIG. 11A, 11B), 2 (FIG. 11E, 11F), 4 (FIGS. 11I, 11J), and 8 (FIG. 11M, 11N) weeks and images of chABC mixed with 3%-$K_{180}L_{20}$ at 1 (FIG. 11C, 11D), 2 (FIG. 11G, 11H), 4 (FIG. 11K, 11L), and 8 (FIG. 11O, 11P) weeks after injection into the CPN on the left side of the brain in WFA and 2B6 stained tissue sections. Note that the digestive capability of chABC alone on CSPGs resolved between 2 and 4 weeks in vivo (FIG. 11E, 11F, 11I, 11J). ChABC mixed with 3%-$K_{180}L_{20}$ was released and showed activity even after 4 weeks in vivo (FIG. 11K, 11L, 11O, 11P).

FIG. 16A shows a transmission electron microscopy (TEM) image of 0.1% $K_{60}L_{20}$ vesicle suspension. FIG. 16B shows a cryogenic TEM image of size-fractionated droplets of $K_{40}(rac-L)_{20}$ stabilized double emulsion. FIG. 16C shows the uptake of FITC-tagged $R_{60}$ (rac-L)$_{20}$ double emulsion into the cytoplasm of cerebral cortical neurons 6 hours after injection in vivo. Scale bars A=350 nm, B=200 nm, C=7 μm

DESCRIPTION

Figure 1:
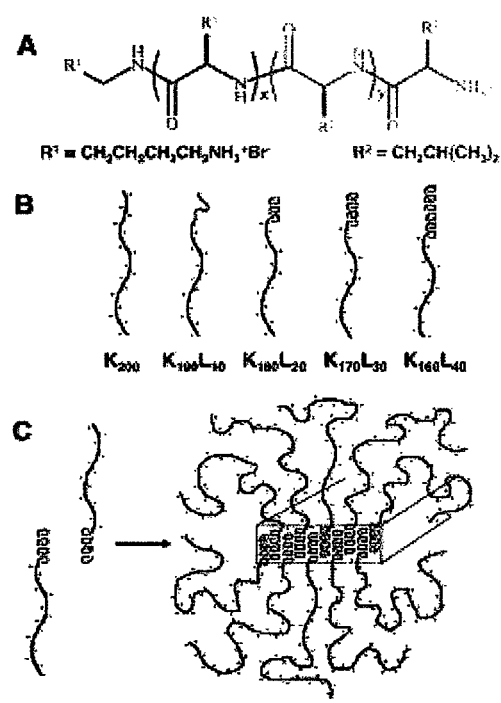
FIG. 1 shows schematic representations of DCH composition and structure.

The present inventors identify formulations of synthetic amphiphilic diblock copolypeptide hydrogels (DCH) that are suitable for use in the central nervous system (CNS), demonstrate methods of making these DHC, and show that the DCH can be used to deliver molecules to specific sites in the CNS (e.g., into cells in the brain or spinal cord). Molecules of interest, such as diagnostic or therapeutic molecules, can be delivered by releasing diffusible biologically active molecules that are mixed with (e.g., dissolved, dispersed, or suspended in) the gel matrix, or that have been conjugated in a reversible or non-reversible fashion to the polypeptide backbone of the DCH. DCH that have been decorated with suitable guides which provide migratory cues (e.g., laminin or bioactive peptides thereof) are also shown to function as extracellular scaffolds, e.g. for the migration of cells, growth of nerve fibers, blood vessel formation, or the like.

The inventors evaluate a variety of block copolymer hydrogel (including diblock copolymer hydrogel, or DCH) formulations, comparing their physical properties in vitro with their properties in vivo after injection into mouse forebrain, and identify some formulations that are particularly suitable for use in the CNS. These formulations are shown to exhibit good biocompatibility with little or no detectable toxicity in the CNS, and can be tuned to exhibit a range of desirable physical properties that make them useful for potential applications in the CNS, as depots or as scaffolds.

The inventors also develop methods for conjugating biologically active molecules (such as peptides or proteins) to DCHs, in a manner such that the biologically active molecules are released in a controlled fashion. The inventors demonstrate, as a representative example, that amphiphilic DCHs can serve as depots for chondroitinase ABC (chABC), and that bioactive chABC can be delivered and released following injection into brain tissue in vivo. Furthermore, the inventors demonstrate that DHCs that have been decorated with migration guidance cues, such as laminin or bioactive peptides thereof (e.g. IKVAV (SEQ ID NO:1) or YIGSR (SEQ ID NO:2)), can serve as scaffolds for, e.g., cell migration and organogenesis in the CNS.

In addition, the inventors show that DHCs can be loaded with nanocarriers (e.g. vesicles or emulsions) that comprise cargo (e.g., nucleic acids, oligonucleotides (such as siRNAs or microRNAs), peptides, oligopeptides, proteins (including enzymes), carbohydrates, viruses, cells, etc.) which can be delivered to and released in a sustained fashion to cells, in vitro and in vivo. Such nanocarriers are particularly useful for entrapping and delivering molecules for which it is desirable to prevent degradation.

Advantages of the DCH of the invention include, e.g., that they are safe, efficacious, have the potential for GMP manufacture, and their production can readily be scaled up to levels required for translational purposes. DCH can easily and reproducibly be produced in large quantities of high purity with complete removal of chemicals employed during synthesis; and the samples are free from pyrogens or biological contaminants and are easily sterilized by autoclave. In addition, they shear thin to liquids during injection and rapidly re-assemble into well-formed deposits that persist in vivo for prolonged periods of time; are biocompatible; and integrate well with host cells and tissues. Such easy to use and well-understood delivery systems can achieve site-specific delivery of bioactive molecules and cells into the brain and spinal cord over controlled periods of time, and can be used in therapeutic strategies for a wide variety of CNS disorders. The unprecedented versatility of these block copolypeptide hydrogen systems provide multiple molecule adjustments to tune different material properties, such as gel strength or porosity.

One aspect of the invention is a composition suitable for administration to the central nervous system (CNS), which comprises a block copolypeptide hydrogel (which is made of a polypeptide backbone in association with an aqueous material, forming a hydrogel). Much of the discussion herein is directed to one type of block copolypeptide hydrogel—a diblock copolypeptide hydrogel (DCH). However, a skilled worker will recognize that the discussion of DCH also applies to other types of block copolypeptide hydrogels. The DCH comprises a biologically active material (sometimes referred to herein as a bioactive material, a bioactive molecule, or a biomolecule) that is (a) mixed with (e.g., suspended in, dispersed in, or dissolved in) the aqueous pores or the hydrogel matrix portion of the DCH, and/or (b) attached (e.g., covalently attached) to the polypeptide backbone of the hydrogel. Such a composition, which is sometimes referred to herein as a "composition of the invention," is suitable for administration to the CNS. A composition of the invention can be used as a depot to deliver a diagnostic or therapeutic agent intracellularly to the brain or spinal cord, or it can serve as a scaffold for, e.g., cell migration, organogenesis, nerve fiber growth and/or blood vessel formation.

In one embodiment of the invention, the biologically active material is a diagnostic or therapeutic agent that is mixed with the DCH. The DCH acts as a depot for that material.

In another embodiment of the invention, the biologically active material is covalently bound to the polypeptide backbone of a DCH, reversibly or non-reversibly. The biologically active material can be, e.g., a peptide, polypeptide, sugar, oligosaccharide, polysaccharide, glycoprotein, or oligonucleotide. The biologically active material can be, e.g., a therapeutic agent or a diagnostic agent (e.g., an MRI contrast agent (such as Gd3+ ions, which can be used for MRI imaging), a radioisotope or a fluorescent probe). The DCH can act as a depot for the covalently attached material.

In another embodiment of the invention, the biologically active material is a peptide or polypeptide which is covalently attached to the polypeptide backbone of the DCH; and the peptide or polypeptide functions as a migration guidance cue. Examples of such peptides or polypeptides include a laminin or a biologically active peptide thereof, such as, e.g., IKVAV (SEQ ID NO:1), or YIGSR (SEQ ID NO:2).

In another embodiment of the invention, the biologically active material is a diagnostic or therapeutic agent that is entrapped in a nanocarrier (e.g., a submicron particle, such as a vesicle, an emulsion, or a double emulsion droplet) which, in turn, is mixed with a block copolypeptide hydrogel of the invention. A double emulsion droplet comprises a mixture of hydrophilic and hydrophobic regions and, itself, can be taken up by a cell.

In any of the compositions of the invention, the block copolypeptide can be a diblock copolypeptide, which may comprise or consist essentially of, e.g.:

poly-L-leucine (L), poly-L-isoleucine (I), poly-L-phenylalanine (F), poly-L-alanine (A), or poly-L-valine (V), or a mixture of these amino acids, as a hydrophobic domain, and poly-L-lysine (K), poly-L-ornithine (O), poly-L-arginine (R), poly-L-homoarginine ($R^H$) or poly-L-glutamate (E), or a mixture of these amino acids, as a hydrophilic domain; or poly-D-leucine (L), poly-D-isoleucine (I), poly-D-phenylalanine (F), poly-D-alanine (A), or poly-D-valine (V), or a mixture of these amino acids, as a hydrophobic domain, and poly-D-lysine (K), poly-D-ornithine (O), poly-D-arginine (R), poly-D-homoarginine ($R^H$) or poly-D-glutamate (E), or a mixture of these amino acids, as a hydrophilic domain; or poly-L-leucine (L) as a hydrophobic domain, and racemic poly-D/L-lysine (rac-K) as a hydrophilic domain; or poly-L-leucine (L) as a hydrophobic domain and poly-L-lysine (K) as a hydrophilic domain; or $K_{180}L_{20}$ (SEQ ID NO:8).

Another aspect of the invention is a method for making a composition of claim 1, comprising covalently attaching a peptide or protein of interest to the polypeptide backbone, by a) thiolating the peptide or protein of interest,
  alkene-functionalizing a group of the polypeptide backbone, and
  thiol-ene coupling (TEC) a thiolated group of the peptide or protein which has been thiolated to an alkene-functionalized group of the polypeptide backbone, or b) thiolating a group of the polypeptide backbone,
  alkene-functionalizing the peptide or protein of interest, and
  thiol-ene coupling (TEC) a thiolated group of the polypeptide backbone which has been thiolated to an alkene-functionalized group of the peptide or protein.

Another aspect of the invention is a method for introducing biologically active chABC into a brain (e.g., a forebrain) in vivo, comprising injecting a composition of the invention in which chABC is mixed with the DCH or is covalently attached to the polypeptide backbone into the brain (e.g., forebrain).

Another aspect of the invention is a method for providing a scaffold for cell migration in the central nervous system (CNS), comprising functionalizing a diblock copolypeptide hydrogel of the invention with a protein or peptide that provides a migration guidance cue (e.g. a laminin or a biologically active peptide thereof).

Another aspect of the invention is a method for stimulating cell migration, or angiogenesis, or for stimulating the ingrowth of nerve fibers, in a brain, comprising introducing into the brain a scaffold that is produced as above. Such a method can, e.g., enhance axonal plasticity and/or improve functional recovery after peripheral nerve repair following spinal cord injury.

Another aspect of the invention is a kit for performing one or more of the methods of the invention, comprising: (a) a block copolypeptide of claim 1, which has been lyophilized, and, optionally, an aqueous solution comprising a therapeutic agent, an imaging agent, or a submicron particle encapsulating an agent of interest, with which the lyophilized block copolypeptide can be reconstituted; or (b) a block copolypeptide of claim 1, which been chemically functionalized with a biomolecule of interest and which has been lyophilized, and, optionally, an aqueous solution with which the functionalized, lyophilized block copolypeptide can be reconstituted.

"CNS" refers to the central nervous system, and includes the brain and spinal cord.

A "biologically active material" (sometimes referred to herein as a bioactive molecule or agent), as used herein, is a material that exhibits a measurable amount of a biological activity. For example, a diagnostic agent can exhibit the ability to stain or image a region of interest; a therapeutic agent can inhibit a symptom of a pathological condition; and a migration guidance cue can provide a signal for a cell to migrate. A biologically active peptide from a protein (e.g., a peptide sequence from a laminin) retains at least one biological activity of the full-length protein (e.g., the ability to provide a migration guidance cue). By a "migration guidance cue" is meant the ability to direct the migration of cells in space or tissue.

By "suitable for administration to the CNS" is meant that the composition is compatible with (e.g., exhibits minimal toxicity, gliosis, or inflammation) to the cells/tissues in the CNS to which it is administered. A composition that is suitable for administration to the CNS may also exhibit one or more of the following advantageous properties: (a) the rheological property of thinning while under shear (e.g., extrusion through a small gauge needle), for ease of processing, but then is able to return immediately via self-assembly after cessation of shear; (b) the completely peptidic nature of the molecular blocks provides an opportunity for facile incorporation of specific secondary structures (e.g., hydrophobe conformation) to manipulate gelatin conformation, by changing which amino acids are in the diblock, relative block lengths, etc.); and (c) degradation over time in vivo to release the depot.

By "minimally cytotoxic" is meant maintenance of cell viability as compared to a suitable control, e.g., as determined using the assays described in the Examples below.

As used herein, the singular forms "a," "an" and "the" include plural referents unless the context clearly dictates otherwise. For example, "a" DCH includes multiple DCH, e.g. 2, 3, 4, 5 or more DCH, which can be the same or different.

A "subject," as used herein, includes any animal that contains an CNS. Suitable subjects (patients) include laboratory animals (such as mouse, rat, rabbit, or guinea pig), farm animals, and domestic animals or pets (such as a cat or dog). Non-human primates, including human patients, are included.

A "therapeutic effect," as used herein, refers to a therapeutic response, such as the amelioration of a symptom associated with a pathological condition or disease, particularly a neurological condition of the CNS. A therapeutic effect can, for example, comprise the prevention, reduction, treatment or elimination of a particular condition. As used herein, an "effective" amount refers to an amount that can bring about at least a detectable (measurable) amount of a desired response of interest. As used herein, a "therapeutically effective amount" refers to an amount that can bring about at least a detectable therapeutic effect.

The amphiphilic block copolypeptides of the present invention comprise at least two distinct polypeptide segments (sometimes referred to herein as blocks, domains, or moieties), which are covalently linked: (1) one or more hydrophilic moieties, sometimes referred to herein as water-soluble, soluble, polar, or charged (anionic or cationic) moieties, and (2) one or more hydrophobic moieties, sometimes referred to herein as a water-insoluble, insoluble, lipophilic, or non-polar moieties.

When one each of a distinct hydrophilic block and a distinct hydrophobic block is present in a copolypeptide, the polypeptide is referred to as a "diblock" copolypeptide. A diblock copolypeptide hydrogel is abbreviated herein as "DCH." When one additional hydrophilic or hydrophobic block (particularly one additional hydrophilic block) is present, the polypeptide is referred to as a "triblock" copolypeptide. Additional segments can be present, e.g., 4, 5 or more segments. Much of the discussion herein is directed to DCH. However, it will be evident to a skilled worker that the discussion also applies to other forms of block copolypeptide hydrogels.

The hydrophilic block(s) of the copolypeptides comprise amino acids with charged side-chains, with the amino acids being, for example: glutamic acid (E), aspartic acid (D), arginine (R), homoarginine ($R^H$), histidine (H), lysine (K), or ornithine (O). The amino acids can be naturally occurring amino acids or D-isomers. Racemic mixtures of D- and L-amino acids are included. In one embodiment, the hydrophilic block is made up of identical amino acids, to form a homopolypeptidic domain. In another embodiment, the hydrophilic domain is made up of two or more different amino acids, which can be mixed in any ratio, to form a heteropolypeptidic domain. In general, a hydrophilic block of the invention contains only polar amino acids. However, in embodiments of the invention, a few non-polar amino acids may also be present, but they must be present in less than about 10% of the total number of amino acids. In embodiments of the invention, the hydrophilic block comprises:

poly-L-lysine (K), poly-L-ornithine (O), poly-L-arginine (R), poly-L-homoarginine ($R^H$) or poly-L-glutamate (E), poly-L-aspartic acid (D), poly-L-histidine (H), or mixtures of these amino acids; or poly-D-lysine (K), poly-D-ornithine (O), poly-D-arginine (R), poly-D-homoarginine ($R^H$), or poly-D-glutamate (E), poly-D-aspartic acid (D), poly-D-histidine (D), or mixtures of these amino acids; or racemic poly-D/L-lysine (rac-K); or poly-L-lysine (K).

The hydrophobic block(s) comprise amino acids with non-ionic (non-polar) side-chains, with the amino acids being, for example: phenylalanine (F), leucine (L), valine (V), isoleucine (I), alanine (A), serine (S), threonine (T) or glutamine (Q). The amino acids can be naturally occurring amino acids or D-isomers. Racemic mixtures of D- and L-amino acids are included. In one embodiment, the hydrophobic block is made up of identical amino acids, to form a homopolypeptidic domain. In another embodiment, the hydrophobic domain is made up of two or more different amino acids, which can be mixed in any ratio, to form a heteropolypeptidic domain. In general, a hydrophobic block of the invention contains only non-polar amino acids. However, in embodiments of the invention, a few polar amino acids may also be present, but they must be present in less than about 10% of the total number of amino acids.

In embodiments of the invention, the hydrophobic block comprises:

poly-L-leucine (L), poly-L-isoleucine (I), poly-L-phenylalanine (F), poly-L-alanine (A), or poly-L-valine (V), poly-L-serine (S), poly-L-threonine (T), poly-L-glutamine (Q), or mixtures of these amino acids; or poly-D-leucine (L), poly-D-isoleucine (I), poly-D-phenylalanine (F), poly-D-alanine (A), or poly-D-valine (V), poly-D-serine (S), poly-D-threonine (T), poly-D-glutamine (Q), or a mixtures of these amino acids; or poly-L-leucine (L).

The length of a copolypeptide chain of the invention is generally between about 100-600 amino acid residues, e.g., about 100, 200, 300, 400, 500 or 600 residues. In one embodiment, which is exemplified herein, the polypeptide chain is about 200 amino acids in length.

The ratio of hydrophilic to hydrophobic amino acids in a copolypeptide chain of the invention can range from about 50-95 mole %. For example, in a diblock copolypeptide of 200 amino acids, the hydrophobic block can be 100-190 amino acids, and the hydrophilic block, 100-10 amino acids, respectively.

The term "about," as used herein, with regard to lengths of biological molecules, amounts of a component of a reaction mixture, etc. means plus or minus 10%.

Some typical block copolypeptides of the invention, and some of their physical properties, are shown in Table 1.

TABLE 1

Gelation concentration and gel strength In both DI water and 100 mM NaCl for a variety of $K_mL_n$ and $E_m L_n$ block copolypeptide samples.

| Sample | Gelation conc (wt %) | Gel Strength | Gel Strength 100 mM NaCl |
|---|---|---|---|
| $K_{80}L_{20}$ | no gel at 6% | NA | NA |
| $K_{190}L_{10}$ | no gel at 5% | NA | NA |
| $K_{180}L_{20}$ | 2% | 12 Pa | 26 Pa |
| $K_{170}L_{30}$ | 0.75% | 590 Pa | 519 Pa |
| $K_{160}L_{40}$ | 0.25% | 4273 Pa | 299 Pa |
| $K_{380}L_{20}$ | 0.25% | 146 Pa | 158 Pa |
| $K_{370}L_{30}$ | 0.031% | 940 Pa | 380 Pa |
| $K_{360}L_{40}$ | 0.125% | 2600 Pa | 242 Pa |
| $E_{180}L_{20}$ | 0.5% | 124 Pa | 469 Pa |
| $E_{160}L_{40}$ | 0.25% | 265 Pa | 47 Pa |
| $K_{190}L_{20}K_{90}$ | 2.5% | 24 Pa | 59 Pa |
| $K_{190}L_{20}K_{190}$ | 0.50% | 420 Pa | 340 Pa |
| $K_{185}L_{30}K_{90}$ | 0.75% | 370 Pa | 460 Pa |
| $K_{185}L_{30}K_{185}$ | 0.40% | 1040 Pa | 230 Pa |
| $K_{80}L_{40}K_{80}$ | 0.75% | 700 Pa | 290 Pa |
| $K_{135}L_{40}K_{135}$ | 0.25% | 3670 Pa | 1200 Pa |
| $K_{180}L_{40}K_{90}$ | 0.25% | 4000 Pa | 880 Pa |
| $K_{180}L_{40}K_{180}$ | 0.25% | 8650 Pa | 1300 Pa |
| $R_{170}L_{30}$ | 0.25% | 8650 Pa | 1300 Pa |
| $K_{160}(rac-L)_{40}$ | 2.5% | 36 Pa | NA |

All gel strengths were measured for 3.0 wt % solutions at 1 rad/s. NA = experiments not performed These block copolypeptides, reading from the top to the bottom of the table, are represented by SEQ ID NO:6-SEQ ID NO:25.

In one embodiment of the invention, the block copolypeptide is the diblock copolypeptide, $K_{180}L_{20}$ (SEQ ID NO:8).

DCHs of the invention are made by allowing block copolymers to self-assemble in an aqueous solution under suitable conditions to form rigid hydrogels. Generally, the pH of the aqueous medium is about pH 4-10, e.g., about pH 6-8; the temperature is about 4° C.-100° C.; and the concentration of the polypeptide is very low (e.g., between about 0.01%-30%, or between about 0.1%-5% (wt % (g/vol), or weight/volume)). Some typical methods of generating DCHs of the invention, and important parameters for forming the desired rigid hydrogels, are discussed in the Examples.

Where a range of values is provided in the present application, it is understood that each intervening value, to the tenth of the unit of the lower limit unless the context clearly dictates otherwise, between the upper and lower limit of that range and any other stated or intervening value in that stated range, is encompassed within the invention. The end values of any range are included in the range.

The amount of copolymer present in the mixture may vary. In certain embodiments the amount of copolymer present in the mixture ranges from about 0.1% weight/volume (w/v) to about 5%, such as from about 0.5 to about 3% and including from about 1 to about 2%.

The nature of the aqueous medium used to generate DCHs of the invention is a function of what biologically active agents, if any, are to be encapsulated in the DCHs. Some typical bioactive agents that can be included in the aqueous medium, and thus encapsulated in the hydrogels, are described below. The concentration of a bioactive agent (e.g., a water-soluble active agent) may vary. In certain embodiments the concentration of active agent present in the mixture ranges from about 1 nM to about 100 mM, such as from about 1 μM to about 100 μM. This concentration will also depend on the potency of the active agent. A variety of acceptable aqueous media will be evident to a skilled worker. These include, e.g., sterilized and/or dionized water, buffers (such as PBS), physiological saline, artificial cerebral spinal fluid, or cell culture media (DMEM).

A block copolypeptide hydrogel of the invention has a heterogeneous microstructure with distinct domains of hydrogel matrix (on the nanoscale) and aqueous (e.g. pure water) pores (on the microscale), as a porous, interconnected membranous network of assembled polypeptides. The elastic gels formed by the netwok of polypeptide chains are suitable for integration into host cells. FIG. 1 illustrates the structure of DCH of the invention.

The polypeptide component of a DCH is sometimes referred to herein as the "polypeptide backbone."

DCH can be deformed by stress, such as extrusion through a small gauge needle, allowing them to be injected as liquids that rapidly re-assemble into gels. DCH are synthesized using chemical polymerization, thus obtainable in pure form with no biological contaminants, and are easily manipulated to achieve different properties for potential applications with different requirements, while retaining basic attributes. The components and properties of DCH can be varied intentionally to achieve different attributes when injected in vivo by, for example, varying the amino acid composition of the copolypeptide blocks, the ratios of hydrophobic and hydrophilic components of the amphiphiles, and/or the concentration of the DCH formulations, which affect gel strengths of the DCH preparations. By varying several factors, one can enable either easy diffusion through tissue, or the provision of three-dimensional (3D) structure to replace lost tissue or bridge cavities.

The polypeptide backbone of DCH allows straightforward incorporation of peptidic functionality that can, e.g., provide a depot of a diagnostic or therapeutic agent which can subsequently be released and delivered into a cell, or which can impart cell adhesion, molecular signaling or enzymatic degradability, either by direct incorporation of desired amino acids into the primary polypeptide chain, or by attaching sequence specific peptides at defined locations on the chains so that bioactive groups can be linked to the polypeptide chains with controlled density and spatial resolution.

Typical methods for covalently attaching peptides or proteins to a polypeptide backbone of a DCH are described in Example II. For example, amine-coupling or thiol-ene coupling can be used to generate irreversible bonds. In some embodiments of the invention, it is desirable to include a reversible (cleavable) crosslinker, a variety of which will be evident to a skilled worker. For example, 4-allyloxy-4-oxobutanoic acid has an alkene group on one end that can be used for thiol-ene coupling to thiolated proteins, and its other end is a carboxylic group that can be coupled to the $N_\epsilon$-amine on the side chain of lysine in DCH. There is an ester group in the middle of the linker that should hydrolyze slowly over time under physiological conditions. Other cleavable cross-linkers will be evident to a skilled worker. These include, e.g., disulfide bonds which will cleave upon reduction. Other molecules that can be attached to a polypeptide backbone (e.g., MRI contrast agents, radioisotopes or fluorescent probes, or other molecules described herein) can be attached using identical chemistry (i.e. either amide bond formation if the molecule has an amine or carboxylate group (non-cleavable), or using the thiol-ene chemistry by attaching either a thiol or alkene to the molecule of interest).

A variety of types of cargo/payload can be loaded into DCH of the invention. The loading can be performed in a non-covalent manner such that the agent is dissolved or dispersed within the polar medium, is associated with the DCH through a non-covalent relationship with the matrix of the hydrogel, is embedded in the hydrogel, or combinations thereof. In other embodiments, one or more of the self-assembling block copolypeptides of a DCH may be covalently modified with an agent of interest. When covalently attached, the agent may be attached to a residue of the polypeptide backbone through a biodegradable bond, such as a disulfide or ester, which bond may include a linker or spacer on either or both sides. In some embodiments, the DCH may include both covalent and non-covalently attached agents of interest, as well as single and multiple different payloads, depending on a given end use.

Some types of cargo to be delivered are hydrophilic, and thus can be readily loaded in a non-covalent manner into the polar interior of a DCH. These water-soluble agents include, e.g., peptides or proteins (such as growth factors, cytokines, function-blocking hybrid proteins, and certain enzymes), peptidomimetics, nucleic acids, oligonucleotides (such as siRNAs, antisense DNA molecules, microRNAs, etc), nucleotides, nucleosides, carbohydrates, and a variety of diagnostic agents, and therapeutic or prophylactic agents, including anti-bacterial agents, anti-viral agents, and cognition enhancers.

Polar cargo, such as, e.g., steroids, sterols, dyes such as 5-dodecanoylaminofluorescein, and certain drugs, can also be introduced into DCH of the invention. For example, a hydrophobic cargo if interest can be attached covalently or admixed with a suitable amphiphilic surfactant for its dispersion or containment in a polar medium suitable for encapsulation into a DCH of the invention. Examples of amphiphilic surfactants for this purpose include, for instance, polyethoxylated fatty acids, such as the PEG-fatty acid monoesters and diesters of lauric acid, oleic acid, and stearic acid (as well as PEG-glycerol fatty acid esters of lauric acid, oleic acid, and stearic acid), amphiphilic transesterification products of oils and alcohols, sterols and sterol derivatives, oil-soluble vitamins. such as vitamins A, D, E, K, etc., polyglycerol esters of fatty acids as well as mixtures of surfactants such as propylene glycol fatty acid esters and glycerol fatty acid esters, amphiphilic esters of sugars such as sucrose monopalmitate and sucrose monolaurate, sucrose monostearate, sucrose distearate, amphiphilic esters of lower alcohols (C2 to C4) and fatty acids (C8 to C8) and the like.

Active biological agents can also be loaded into a DCH of the invention by encapsulating them first in a nanocarrier, such as a vesicle, emulsion, or a double emulsion droplet. Further discussions of how to generate and load such vesicles, and representative examples of biologically active molecules that can be loaded in such nanocarriers, can be found in Example V, and in co-pending US applications: publication number 2010/0003336, filed May 29, 2009; application Ser. No. 12/595,800, filed Oct. 13, 2009; and application Ser. No. 12/231,914, filed Feb. 20, 2009, each of which is incorporated by reference herein in its entirety.

Compositions of the invention can be used in a variety of ways, in vitro or in vivo, including, e.g., research applications, the formation of scaffolds which support cell migration, or restricted targeting of diffusible molecules for the diagnosis of neurological conditions (e.g., imaging technology) or for the delivery of therapeutic agents to treat neurological conditions.

DCH of the invention can deliver agents that can facilitate research applications, such as cell-based assays (e.g., intracellular delivery of ion indicators, reactive dyes and chemicals, or primary or secondary detection and/or quantitation components).

DCH of the invention can deliver agents to the CNS for diagnostic purposes, such as imaging and contrast agents. Suitable diagnostic agents include, e.g., a detectable label or a reporter ligand, which includes both active and passive reporter ligands such as a component of a fluorescence resonance energy transfer (FRET) detection system, spin-trap agents, quantum dots, chelated agents, contrast agents, dyes, radiolabels, peptides, nucleic acids, antibodies, antibody fragments and the like. DCH loaded with diagnostic agents can be used in connection with a variety of detection and imaging modalities, such as those involving standard analytic and/or separation-based detection modalities (e.g., chromatography, Enzyme-Linked ImmunoSorbent Assays (ELISA) etc.), as well as those based on less invasive modalities such as gamma-scintigraphy, magnetic resonance imaging and computed tomography).

For example, DCH can be loaded with chelated or bifunctional chelated agents (e.g., covalent linkage group coupled to a targeting moiety such as an antibody, antibody fragment, peptide or hormone and a chelating group for the metal) and used (depending on the particular agent selected and modality of administration) for, e.g., myelography (radiological study of the spinal cord); CAT scan (Computerized Axial Tomography as a method of resolution of a series of x-ray pictures into a "cross-section" of the body or part of the body, such as the brain, in which a contrast agent may be employed), NMR scan or MRI (Magnetic Resonance Imaging as a computerized method of resolution of a series of radio-frequency scans of tissues into a "cross-section" of the body or body part, such as the brain, which visualizes in a tissue-specific manner the composition of areas rather than density as in the CAT scan).

In one embodiment of the invention, the diagnostic agent employs technecium. This agent is used in 85% of all medical diagnostic scans, easily forms metal-electron donor complexes or chelates in the presence of a reducing agent, such as electronegative chelating groups illustrated by SH thiols, $CO_2$-carboxylates, NH amines, $PO_4$-phosphate, CNOH oximes, OH hydroxyls, P phosphines, and NC isonitriles, exhibits good properties for imaging with a gamma camera, and possesses a short half-life of 6 hours that is adequate to synthesize chelate, determine purity, administer and image with a minimum radiation exposure.

Illustrative chelated agents include technecium tagged agents such as, e.g., technecium biscisate (which can be used, e.g., for imaging to determine brain perfusion in stroke and lesion determination); technecium exametazine (a brain imaging agent to determine brain death in life support patients, localize seizure foci, dementia, strokes); technecium glucetate (e.g., for radiolabeling of monoclonal antibodies); and technecium pentetate (e.g., imaging of the brain for brain tumors and death).

Other radiolabel generators in addition to technecium include complexes of strontium-yttrium, zinc-copper, germanium-gallium, strontium-rubidium, gallium citrate, 18F-2-fluoro-2-deoxy-D-glucose (e.g., PET scanning (positron emission tomography) for determining metabolic rate in the brain, and cancer management (neoplasms have a high glycolytic rate) etc.), iodine radiolabels (e.g., iobenguane sulfate$^{131}$I for imaging and locating functional neuroblastomas), indium radiolabels (e.g., utilized to radiolabel monoclonal antibodies and peptides via bifunctional chelating agents; such as indium chloride which behaves similar to $Fe^3$ for imaging of tumors); indium satumomabpendetide for labeling of monoclonal antibodies; and indium oxine (8-hydroxyquinoline) for replacing gallium radiolabels due to better specificity and better image quality.

Additional diagnostic agents include radiological contrast agents such as the iodine based compounds (e.g., diatrizoate megllumine, distrizoate sodium, iopanoic acid, tryopanoate sodium, ipdoate sodium, iothalamate meglumine, iodipamide meglumine, iohexyl, iopamidol, ioversol, iodixanol, isosulfan blue, pentetreotide), MRI contrast agents (e.g., gadolinium chelated compounds such as gadopentetate dimeglumin, gadoteridol, ferummoxsil, ferumoxides, masngofodipir trisodium), and ultrasound contrast agents (e.g., perflexane-n-perfluorohexane gas, and 1,2-dimyristoyl-sn-glycero-3-phosphocholine (DMPC)).

DCH of the invention can be used as depots for intracellular delivery (e.g., sustained molecular release) of therapeutic (including prophylactic) agents. A variety of suitable therapeutic agents will be evident to a skilled worker. These include, e.g., growth factors, cytokines, function-blocking hybrid proteins, inhibitors, certain enzymes, oligonucleotides (such as siRNAs, antisense DNA molecules, microRNAs, etc), anti-bacterial agents, anti-viral agents, cognition enhancers, etc. Example II describes the loading and delivery of one representative therapeutic agent, chondroitinase ABC (chABC), in a DCH of the invention. Other therapeutic agents (polypeptide-based, polynucleotide-based, etc.) will be evident to a skilled worker. Some suitable agents are listed in co-pending application 2010/0003336, which is incorporated by reference in its entirety herein.

DCH of the invention can be used to provide extracellular matrices (scaffolds) to support and guide cell migration in the CNS. For example, such a scaffold can bridge cell and nerve fiber migration across scar tissue or to fill wound cavities; can support axon growth; or can support grafted cells. Neural stem/progenitor cell grafts hold promise for replacing lost cells in certain neurological conditions (e.g. neurodegenerative diseases, such as multiple sclerosis, or stroke), but most current grafting procedures are regarded as resulting in suboptimal survival and differentiation of cells. Compositions of the invention can improve grafting efficiency by providing grafted cells with support matrix and molecular substrates that help them overcome the shock of the grafting procedure and integrate and differentiate better in to host tissue.

In embodiments in which the DCH are used as scaffolds, polypeptide chains of the DCH are functionalized with appropriate migration guidance cues, examples of which will be evident to a skilled worker. Such cues include, e.g., the alpha chain of laminins or active peptides thereof, such as ile-lys-val-ala-val, or IKVAV (SEQ ID NO:1); tyr-ile-gly-ser-arg, or YIGSR (SEQ ID NO:2); ser-ile-lys-val-ala-val (SIKVAV) (SEQ ID NO:3); RNIAEIIKDI (SEQ ID NO:4); and SRARKQAASIKVAVSADR (SEQ ID NO:5). Other suitable migration cues will be evident to a skilled worker. These include, e.g., whole growth factors such as BNDF, NT3, or NGF. For a further discussion of this embodiment of the invention, see Example III herein.

The compositions discussed herein can be formulated into various compositions, for use in diagnostic or therapeutic treatment methods. The compositions (e.g. pharmaceutical compositions) can be assembled as a kit. Generally, a pharmaceutical composition of the invention comprises an effective amount (e.g., a pharmaceutically effective amount) of a composition of the invention.

A composition of the invention can be formulated as a pharmaceutical composition, which comprises a composition of the invention and pharmaceutically acceptable carrier. By a "pharmaceutically acceptable carrier" is meant a material that is not biologically or otherwise undesirable, i.e., the material may be administered to a subject without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art. For a discussion of pharmaceutically acceptable carriers and other components of pharmaceutical compositions, see, e.g., Remington's Pharmaceutical Sciences, $18^{th}$ ed., Mack Publishing Company, 1990. Some suitable pharmaceutical carriers will be evident to a skilled worker and include, e.g., water (including sterile and/or deionized water), suitable buffers (such as PBS), physiological saline, cell culture medium (such as DMEM), artificial cerebral spinal fluid, or the like.

A pharmaceutical composition or kit of the invention can contain other pharmaceuticals, in addition to the compositions of the invention. The other agent(s) can be administered at any suitable time during the treatment of the patient, either concurrently or sequentially.

One skilled in the art will appreciate that the particular formulation will depend, in part, upon the particular agent that is employed, and the chosen route of administration. Accordingly, there is a wide variety of suitable formulations of compositions of the present invention.

Formulations which are suitable for topical administration directly in the CNS include, e.g., suitable liquid carriers, or creams, emulsions, suspensions, solutions, gels, creams, pastes, foams, lubricants, or sprays. Topical administration in the CNS is possible when the CNS is opened by wound or during a surgery.

One skilled in the art will appreciate that a suitable or appropriate formulation can be selected, adapted or developed based upon the particular application at hand.

Dosages for compositions of the invention can be in unit dosage form. The term "unit dosage form" as used herein refers to physically discrete units suitable as unitary dosages for animal (e.g. human) subjects, each unit containing a predetermined quantity of an agent of the invention, alone or in combination with other therapeutic agents, calculated in an amount sufficient to produce the desired effect in association with a pharmaceutically acceptable diluent, carrier, or vehicle.

One skilled in the art can easily determine the appropriate dose, schedule, and method of administration for the exact formulation of the composition being used, in order to achieve the desired effective amount or effective concentration of the agent in the individual patient.

A variety of suitable routes of administration to the brain or spinal column will be evident to a skilled worker. For example, a composition of the invention can be administered with a catheter or a needle (syringe). In a case in which brain tissue has been exposed (e.g., during open brain surgery), a composition of the invention can be administered directly to the exposed tissue, e.g. by topical administration.

The dose of a composition of the invention, administered to an animal, particularly a human, in the context of the present invention should be sufficient to effect at least a detectable amount of a diagnostic or therapeutic response in the individual over a reasonable time frame. The dose used to achieve a desired effect will be determined by a variety of factors, including the potency of the particular agent being administered, the pharmacodynamics associated with the agent in the host, the severity of the disease state of infected individuals, other medications being administered to the subject, etc. The size of the dose also will be determined by the existence of any adverse side effects that may accompany the particular agent, or composition thereof, employed. It is generally desirable, whenever possible, to keep adverse side effects to a minimum.

A suitable dose of a composition of the invention to be administered to the brain is generally determined as a function of the volume of the brain. For example, for a mouse, whose brain has a volume of about 1-2 cc, one generally administers about 1 µL-10 µL of a composition of the invention (having a concentration of about 3% (w/v)). A similar ratio of volume of the composition to the volume of the brain (about 1/2000-1/100) can be used for subjects with larger brains, such as human patients. Because the spinal cord is much smaller than the brain, the dosage to the spinal cord would be about 1/10th to 1/100$^{th}$ of the dosage to the brain. The dose of the biologically active material will vary; suitable amounts for each particular agent will be evident to a skilled worker.

Another embodiment of the invention is a kit useful for any of the methods disclosed herein, either in vitro or in vivo. Such a kit can comprise one or more of the compositions of the invention. Optionally, the kits comprise instructions for performing the method. Optional elements of a kit of the invention include suitable buffers, pharmaceutically acceptable carriers, or the like, containers, or packaging materials. The reagents of the kit may be in containers in which the reagents are stable, e.g., in lyophilized form or stabilized liquids. The reagents may also be in single use form, e.g., in single dosage form.

In one embodiment, the kit comprises a lyophilized block copolypeptide of the invention, and, optionally, one or more suitable molecules in aqueous solution (e.g., a solution comprising a therapeutic agent or an imaging agent, or a submicron particle, such as a vesicle or a double emulsion droplet, which encapsulates an agent of interest). The block polypeptide can then be reconstituted with the aqueous solution to form a hydrogel.

In another embodiment, the kit comprises a lyophilized block copolypeptide of the invention which has been chemically functionalized with a biomolecule of interest and, optionally, an aqueous solution with which the lyophilized block copolypeptide can be reconstituted.

A skilled worker will recognize components of kits suitable for carrying out any of the methods of the invention.

In the foregoing and in the following examples, all temperatures are set forth in uncorrected degrees Celsius; and, unless otherwise indicated, all parts and percentages are by weight.

EXAMPLES

Example I

Biocompatibility of Amphiphilic Diblock Copolypeptide Hydrogels in the Central Nervous System A. Summary Amphiphilic diblock copolypeptide hydrogels (DCH) are synthetic materials whose properties can be varied readily and predictably by altering copolymer chain length or composition and which are of potential interest for biomaterial applications. We tested the biocompatibility in the central nervous system (CNS) of DCH composed of lysine, homoarginine or glutamate in combination with leucine. A range of DCH formulations with rheological properties similar to brain tissue were injected into mouse forebrain and examined after 1 to 8 weeks using light microscopy, immunohistochemistry and electron microscopy, DCH deposits elicited no more gliosis, inflammation, or toxicity to neurons, myelin or axons than did injections of physiological saline. The size, rigidity, and density of DCH deposits could be varied subtly by altering DCH composition and concentration. For any given DCH formulation, increased concentration correlated with increased gel strength in vitro and increased deposit size in vivo. DCH of lysine and leucine ($K_m L_n$) were selected for detailed analyses because these formed deposits with desirable physical properties and since lysine is routinely used as a substrate for neural cell cultures. Deposits of unmodified $K_{180}L_{20}$ exhibited time dependent in-growth of blood vessels and of certain glial cells, and limited in-growth of nerve fibers. These findings show that DCH are injectable, reassemble in vivo to form 3-dimensional deposits, are biocompatible in brain tissue and represent a new class of synthetic biomaterials with potential for applications as depots or scaffolds in the CNS.

B. Methods

1. Design of DCH Formulations Tested in vivo

DCH with different properties can be prepared by varying amino acid compositions, chain lengths, and by conjugation of molecules with specific properties to amino acid side-chain functional groups (FIG. 1A,B) (Nowak et al. (2002) (supra); Deming (2005) (supra)). We have reported previously that block copolypeptides containing polyelectrolyte segments and hydrophobic helical domains can stabilize formation of hydrated membranes and fibrils that form a robust hydrogel network (Deming (2005) (supra)). The assembly mechanism, elucidated via analysis of structure-property relationships and the use of a range of characterization tools (Pochan et al. (2002), SANS and cryo-TEM study of self-assembled diblock copolypeptide hydrogels with rich nano-through microscale morphology, *Macromolecules* 35, 5358-5360; Breedveld et al. (2004) (supra)), was found to occur via association of α-helices perpendicular to fibril/membrane long dimensions (FIG. 1C).

In the present Example, we prepared DCH samples 200 residues long, on average, in which the ratio of hydrophilic to hydrophobic amino acids was varied (FIG. 1B,C) to achieve different gelation strengths based, in part, on past experience (Nowak et al. (2002) (supra); Deming (2005) (supra)). We used poly-L-leucine (L) as the hydrophobic domain, and tested poly-L-lysine (K) as the hydrophilic domain exposed to tissue, because it is a widely used substrate in neural cell cultures that is well tolerated by neural cells (Yavin et al. (1974) Attachment and culture of dissociated cells from rat embryo cerebral hemispheres on polylysine-coated surface, *J Cell Biol* 62, 540-546; Svendsen et al. (1994), Death of developing septal cholinergic neurons following NGF withdrawal in vitro: Protection by protein synthesis inhibition, *J Neurosci* 14, 75-87; Sanjana et al. (2004), A fast flexible ink-jet printing method for patterning dissociated neurons in culture, *J Neurosci Methods* 136, 151-163)). We also prepared DCH with poly-L-homoarginine (R) or poly-L-glutamate (E) as the hydrophilic domain. In addition, we conjugated lysine based DCH with fluorescent dye to track their location in host tissue.

2. Synthesis of DCH a. Materials and instrumentation. Tetrahydrofuran (THF), hexanes, and methylene chloride were dried by purging with nitrogen and passage through activated alumina columns prior to use (Pangborn et al. (1996), Safe and convenient procedure for solvent purification, *Organometallics* 15, 1518-152). Co(PMe$_3$)$_4$ was prepared according to literature procedures (Klein et al. (1975), Methylcobalt compounds with non-chelating ligands I. Methyltetrakis(trimethylphosphine) cobalt and its derivatives. *Chemische Berichte* 108, 944-955). Trimethyliodosilane (TMIS) was purified by distillation and stored over copper shot prior to use. All other chemicals were purchased from commercial suppliers and used without further purification unless otherwise noted. Fourier Transform Infrared (FTIR) measurements were taken on a Perkin Elmer RX1 FTIR spectrophotometer calibrated using polystyrene film. $^1$H NMR spectra were acquired on Bruker ARX 400 spectrometer. Tandem gel permeation chromatography/light scattering (GPC/LS) was performed at 60° C. using an SSI Accuflow Series III pump equipped with Wyatt DAWN EOS light scattering and Optilab rEX refractive index detectors. Separations were achieved using $10^5$, $10^4$, and $10^3$ Å Phenomenex Phenogel 5 μm columns with 0.1 M LiBr in DMF as eluent and sample concentrations of 5 mg/mL. Pyrogen free deionized water (DI) was obtained from a Millipore Milli-Q Biocel A10 purification unit.

b. General polypeptide synthesis. All block copolypeptides were synthesized using Co(PMe$_3$)$_4$ initiator, according to literature procedures (Deming (1999), Cobalt and iron initiators for the controlled polymerization of alpha-amino acid-N-carboxyanhydrides, *Macromolecules* 4500-4502; Nowak et al. (2002) (supra). Protected copolypeptides were purified, and then characterized using tandem GPC/LS and FTIR. The protecting groups of N$_\epsilon$-benzyloxycarbonyl-L-lysine residues were removed to give L-lysine•HBr residues in copolypeptides by addition of 33 wt % HBr in acetic acid to a solution of copolymer in trifluoroacetic acid (TFA) at 0° C. for 1 hour. Poly(γ-benzyl-L-glutamate)-containing diblocks were deprotected using TMIS in CH$_2$Cl$_2$ at 40° C. for 36 hours. All deprotected copolymers were dissolved in and then dialyzed exhaustively against nonpyrogenic DI water. Lyophilization of these solutions gave the copolymers as white powders, whose compositions were confirmed using FTIR, $^1$H NMR, and gas chromatography. Isolated yields of the deprotected copolymers ranged between 75% and 90%. Relative copolypeptide compositions were determined using amino acid analysis by gas chromatography and were found to be within 4% of predicted values (Table 2). Chain lengths of K$_m$ and E$_m$ segments were determined using GPC and were found to be within 5% of predicted values with polydispersities (M$_w$/M$_n$) ranging from 1.23 to 1.34. Actual copolypeptide compositions were determined by combining relative compositions from gas chromatography data with K$_m$ and E$_m$ chain lengths from GPC data (Table 2). $^1$H NMR in deuterated TFA (d-TFA) indicated a 97%-98% removal of benzyloxycarbonyl groups from lysine residues.

c. Conversion of K$_{180}$L$_{20}$ (SEQ ID NO:8) to give R$_{180}$L$_{20}$ (SEQ ID NO:26). Homoarginine residues can be obtained by converting the ε-amino groups in lysine side chains to guanidinium groups using O-methylisourea (Kimmel (1967) Guanidination of proteins, *Methods Enzymol* 11, 584-589; Beardsley et al. (2002) Optimization of guanidination procedures for MALDI mass mapping, *Anal Chem* 74, 1884-1890). The typical conversion efficiency is 80-85% yield (Beardsley et al. (2002) Optimization of guanidination procedures for MALDI mass mapping, *Anal Chem* 74, 1884-1890). The guanidinylation reaction mixture was prepared by mixing O-methylisourea solution (3.0 g, 27 mmol of O-methylisourea hydrochloride in 10 mL of DI water, pH adjusted to 10.5) with aqueous K$_{180}$L$_{20}$ solution (160 mg, 3.8 μmol of K$_{180}$L$_{20}$ (SEQ ID NO:8) in 20 mL of pyrogen free water) in a sterilized 100-mL round bottom flask. The final pH was adjusted to 10.5 and the reaction was carried out at 37° C. under stirring for one week. Guanidinylation was terminated by acidifying the solution with hydrochloric acid. The mixture was then transferred to a dialysis bag (Regenerated Cellulose, Spectra/Por, MWCO 6-8 kDa) that was placed in a sterile 4-liter container of pyrogen free water. The water was replaced twice a day for 5 days. The solution was then freeze dried to yield the product as a spongy solid. The extent of guanidinylation was determined with gas chromatography by quantifying the residual lysines in R$_{180}$L$_{20}$ hydrolyzate. The guanidinium groups of homoarginine are not derivatized with ethylchloroformate (ECF), and so these residues do not elute from the column (Husek, 1991). The detailed gas chromatography analysis is described below.

d. Functionalization of K$_{180}$L$_{20}$ (SEQ ID NO:8) to give Texas Red-K$_{180}$L$_{20}$ (SEQ ID NO:8). Fluorescent tagging of lysine-ε-amine groups was performed using Texas Red sulfonyl chloride in DMF (10 mg/mL). K$_{180}$L$_{20}$ (SEQ ID NO:8) powder (130 mg, 3.2 μmol) was dissolved in aqueous NaHCO$_3$ (30 mL, 0.1 M). To the polypeptide solution, 5 equivalents of Texas Red per chain (corresponding to 2.8% of the available lysine amines) were added, and the mixture was stirred for 16 hours. LiBr (1 g) and HCl (500 μl, 12 N) were then added. For purification, the sample, covered in Al foil to protect from light, was dialyzed (MWCO 6-8 kDa) for 5 days with pyrogen free water changed every 12 hours. The functionalized polymer (Texas Red-K$_{180}$L$_{20}$) was isolated by lyophilization to give a slightly yellow powder (130 mg).

3. Gas Chromatography.

Amino acid composition analysis of each DCH sample began with liquid phase hydrolysis followed by chemical derivatization prior to the gas chromatography analysis. Each copolypeptide powder (2-3 mg) was dissolved in concentrated hydrochloric acid (12N, 400 μL) and flame sealed in a 1-mL glass ampoule. The samples were then hydrolyzed in oven at 110° C. for two weeks. Due to the highly associated nature of the hydrophobic poly-L-leucine segments, strong

TABLE 2

Gas Chromatography (GC) of DCH.

| Predicted composition | GPC | PDI | GC Determined composition |
|---|---|---|---|
| K160L40 (SEQ ID: 10) | K158 (SEQ ID: 27) | 1.290 | K158L35 (SEQ ID NO: 33) |
| K170L30 (SEQ ID: 9) | K168 (SEQ ID: 28) | 1.341 | K168L27 (SEQ ID NO: 34) |
| K180L20 (SEQ ID: 8) | K180 (SEQ ID: 29) | 1.298 | K180L21 (SEQ ID NO: 35) |
| K190L10 (SEQ ID: 7) | K191 (SEQ ID: 30) | 1.234 | K191L8 (SEQ ID NO: 36) |
| E180L20 (SEQ ID: 14) | E179 (SEQ ID: 31) | 1.274 | E179L23 (SEQ ID NO: 37) |
| R180L20 (SEQ ID: 26) | K180 (SEQ ID: 32) | 1.298 | (R150K30)L21 (SEQ ID NO: 38) |

GPC—Gel permeation chromatography
PDI—Polydispersity index acidic conditions and long hydrolysis times are essential to fully decompose the polymers into individual amino acid components, where reaction time must be increased with the length of the leucine segments. The hydrolyzates were transferred to 15-mL polypropylene conical tubes. The liquid content of each sample was evaporated and spin dried in a Labconco centrivap concentrator at 80° C. for 2 hours. Derivatization for gas chromatography analysis was modified from the literature procedure (Husek (1991) Rapid derivatization and gas chromatographic determination of amino acids, *J Chromatogr* 1991, 289-299). Dried hydrolyzates were reconstituted in dilute HCl (100 mM, 500 μL) and treated with 700 μl of ethanol-pyridine (4:1 v/v). Next, 100 μL of ECF was added to each tube followed by gently vortexing the tube until the gas evolution stopped. 300 μL of DI water was added to each tube followed by 1000 μl, of toluene. The derivatives were extracted into the organic phase by vortexing and then centrifugation. For each sample, an aliquot of the organic phase (1 μL) was injected into the gas chromatography capillary column (Phenomenex ZB-AAA 10 m×0.25 mm ID Amino Acid Analysis column). A Shimadzu GC-17A gas chromatograph with flame ionization detector (FID) and auto sampler was employed. Sample injection mode (1:15) was used for each analysis. The injector and detector temperatures were 300° C. and 325° C., respectively. The oven temperature was programmed to increase from 110° C. to 320° C. stepwise (32° C./min). Helium was used as the carrier gas with a constant flow rate (1.5 mL/min). Standard calibrations for each amino acid were established using individual amino acid standard with six different concentrations ranging from 0.5 mM to 10 mM using identical derivatization and analysis as the copolypeptide hydrolyzates. Each sample or standard was measured in triplicate.

4. Rheology a. Hydrogel rheology. Block copolypeptide hydrogels were prepared by dissolving freeze-dried samples in DI water. Samples in ionic media, for example artificial cerebral spinal fluid were prepared either by direct dissolution of the sample in the media, or by dissolution of the sample at a higher than target concentration in DI water, followed by dilution with a concentrated solution of the ionic media. Artificial cerebrospinal fluid was prepared according to commonly accepted guidelines (Bocchiaro et al. (2004) Synaptic activity-independent persistent plasticity in endogenously active mammalian motoneurons, *Proc Natl Acad Sci USA* 101:4292-4295). The dissolution process of the samples was enhanced through vortex mixing. Solution properties were identical within experimental limits regardless of sample preparation method. The rheological properties were also not affected by the agitation; identical mechanical properties were obtained by letting the copolypeptides dissolve without mixing over three days. Rheological measurements (dynamic) were performed on a strain controlled Reometrics fluids spectrometer RFS II in a cone-plate geometry with diameter of 25 mm and cone angle of 0.02 rad similar to previously described (Breedveld et al. (2004) (supra). For each sample small-deformation linearity was checked before performing oscillatory measurements.

b. Brain rheology. The shear moduli measurements of mouse brain tissue were modified from a literature procedure (Georges et al. (2006) Matrices with compliance comparable to that of brain tissue select neuronal over glial growth in mixed cortical cultures, *Biophys J* 90, 3012-3018) and performed on the same rheometer as the DCH samples. Mouse brain slices containing striatum at thickness ranging from 1.1 to 1.3 mm were prepared using a vibratome. The edge of each brain slice was trimmed to an approximately round shape with a scalpel. Samples were placed between two 25-mm serrated stainless parallel plates. Serrated plates were used to minimize slipping of the sample on the plate and the tissue was found to stick well to these plates without the need for surgical glue. Tissue samples were relatively uniform in thickness when examined by eye. A normal force sensor attached to the rheometer was useful in determining thickness uniformity in a less qualitative manner. A non-uniform thickness tissue sample would result in portions of the sample contacting the upper plate before others, causing the normal force to be relatively high once the entire tissue was in contact. Non-uniform tissue samples were discarded and other samples from the same tissue were dissected until suitable sections were obtained. Care was taken not to compress the sample greatly. Storage modulus G' was measured by subjecting samples to 1 rads oscillation of 1% shear strain. The testing area was enclosed by a moisture trap and total test time was less than 3 min to minimize dehydration of the samples.

5. In vivo Injections of DCH a. Preparation of DCH for injection. Freeze dried DCH powders were reconstituted to specific concentration on wt/vol basis using double distilled sterile water.

b. Animals. All in vivo experiments were conducted using wild-type C57B16 mice from an in house breeding colony. Mice were housed in a 12 hour light/dark cycle in an SPF facility with controlled temperature and humidity and allowed free access to food and water, and all surgical procedures and experiments were conducted according to protocols approved by the Chancellor's Animal Research Committee of the Office for Protection of Research Subjects at UCLA.

c. Surgical Procedures. All surgical procedures were performed under sterile conditions with isoflurane in oxygen-enriched air as the general anesthesia and using an operating microscope (Zeiss, Oberkochen, Germany),) and rodent stereotaxic apparatus (David Kopf, Tujunga, Calif.) as described (Myer et al. (2006) Essential protective roles of reactive astrocytes in traumatic brain injury, *Brain* 129, 2761-2772). The skull was exposed and a burr hole was drilled with a high speed dental drill. Sterile solutions of DCH or physiological saline were injected stereotaxically into the center of the caudate putamen nucleus using the target coordinates of 1.0 mm posterior to Bregma, 1.5 mm lateral to Bregma and a depth of 3.0 mm below the cortical surface. Analgesic was given prior to wound closure and every 12 hr for 48 hr post-injury.

6. Histological Procedures

At the end of experiments, all mice received terminal anesthesia by barbiturate overdose and were perfused transcardially with phosphate buffered saline (PBS) followed by 10% formalin in PBS. Brains were removed, post-fixed for a further 2 hours and cryoprotected in buffered 30% sucrose overnight. 40 μm coronal frozen sections were prepared using a cryostat microtome (Leica, Nussloch, Germany) and processed for various kinds of histological evaluation as described previously (Myer et al. (2006) (supra). Brightfield immunohistochemistry was performed using biotinylated secondary antibodies (Vector, Burlingame, Calif.), biotin-avidin-peroxidase complex (Vector) and diaminobenzidine (DAB, Vector) as the developing agent. Primary antibodies were: rabbit anti-polylysine (1:5000, Dr. Katopodis (Katopodis et al. (2002) Removal of anti-Galalpha1,3Gal xenoantibodies with an injectable polymer, *J Clin Invest* 110, 1869-1877), rabbit anti-GFAP (1:20,000; Dako, Carpinteria, Calif.), rat anti-GFAP (1:5000, Zymed Laboratories); rat anti-mouse CD45 (1:2000; PharMingen, La Jolla, Calif.); rat anti-CD3 (1:2000; PharMingen, La Jolla, Calif.); mouse anti-NeuN (1:5000 Millipore); rabbit anti-PECAM1 (1:400; PharMingen, La Jolla, Calif.); rabbit anti-NG2 (1:2500; Millipore). Staining with cresyl violet or luxol fast blue was conducted according to standard procedures. Stained sections were examined and photographed using brightfield and fluorescence microscopy (Zeiss, Oberkochen, Germany). The relative sizes of DCH deposits in tissue sections were measured using image analysis software (NeuroLucida®, MicroBrightField, Williston, Vt.) operating a computer-driven microscope regulated in the x, y and z axes (Hemnann et al. (2008) STAT3 is a critical regulator of astrogliosis and scar formation after spinal cord injury, *J Neurosci* 28, 7231-7243). Deposit size was measured as surface area ($\mu m^2$) on the tissue section that contained the central portion of the deposit.

For electron microscopic analysis, mice were perfused, after terminal barbiturate overdose, with buffered 2% paraformaldehyde and 1.0% glutaraldehyde. Tissue blocks were dissected, post-fixed for 24 hours and processed for electron microscopy as described in detail previously (Havton et al. (2005). Briefly, sections were osmicated in 1% osmium tetroxide, dehydrated and plastic-embedded in Epon. Semithin sections were cut, stained with toluidine blue, and examined in the light microscopy to identify biopolymer injection sites. Tissue blocks were trimmed and ultrathin sections (60-70 nm) were serially collected on formvar-coated copper one-hole grids, counterstained with uranyl acetate and lead citrate, and examined in a JEOL 100 CX transmission electron microscope.

C. Results

1. Physical Characterization of DCH

Properties of extracellular materials, such as elasticity and porosity, influence cellular behaviors such as cell migration and nerve fiber growth (Discher et al. (2005) Tissue cells feel and respond to the stiffness of their substrate, *Science* 310, 1139-11433). Brain is among the softest of biological tissues. We compared rheological properties of different DCH formulations with that of our in vivo target tissue, mouse brain, using the same apparatus and conditions. We obtained a mean storage modulus (G') value of 190±22 Pa for mouse forebrain (n=7, Table 3), which is within the range of 100 to 400 Pa found by others for adult rat or pig brain (Miller et al. (2000) Mechanical properties of brain tissue in-vivo: experiment and computer simulation, *J Biomech* 33, 1369-1376; Georges et al. (2006) Matrices with compliance comparable to that of brain tissue select neuronal over glial growth in mixed cortical cultures, *Biophys J* 90, 3012-3018). Table 3 summarizes the G' values of the various DCH formulations examined for this study. As expected from previous studies (Nowak et al. (2002) (supra); Breedveld et al. (2004) (supra)), G' values of DCH varied with the (i) ratio of hydrophilic to hydrophobic residues, (ii) concentration (i.e. weight percent; wt %) of the preparation, and (iii) component amino acids. Previous studies have also shown that increased hydrophobic content generally gives stronger gels at lower polypeptide concentrations in water, but also results in decreased solubility and weaker gels in ionic media for samples with lower charge ratios, but not for samples with higher charge ratios (Nowak et al. (2003) Unusual salt stability in highly charged diblock co-polypeptide hydrogels, *J Am Chem Soc* 125,15666-15670). Consistent with such previous observations, here we also found that addition of salt and other ions to the media, for example as in artificial cerebrospinal fluid, weakened $K_{170}L_{30}$ (SEQ ID NO:9) hydrogels, but increased the storage modulus of $K_{180}L_{20}$ (SEQ ID NO:8) samples (Table 3). The samples shown in Table 3 exhibited a good range of G' values that were able to bracket the value for mouse brain at many different concentrations, allowing evaluation of samples that were mechanically similar but with markedly different porosities. Thus a 0.5 wt % sample of $K_{170}L_{30}$ (SEQ ID NO:9) had a gel strength similar to a 3 wt % sample of $K_{180}L_{20}$ (SEQ ID NO:8) (Table 3). $K_{190}L_{10}$ (SEQ ID NO:7) became extremely viscous at high concentrations but did not form a true gel at concentrations up to 20 wt %. $K_{200}$ (SEQ ID NO:39) was used as non-gelling control. Samples with G' values below that of mouse brain were all easily injectable using small bore cannulae, and consequently were the main focus of this study. For consistency and ease of comparison, DCH administered in vivo were routinely prepared in sterile water. The DCH formulations that were studied after injection in vivo are indicated in boxes in Table 3.

TABLE 3

Rheological measurements of G' (Pa) of brain tissue and DCH (in H20).
Brain (striatum) (190 ± 22)

| Gels | 0.125% | 0.25% | 0.5% | 1% | 2% | 3% | 4% | 5% | 10% |
|---|---|---|---|---|---|---|---|---|---|
| $K_{160}L_{40}$ | fl | 42 ± 4 | 191 ± 5 | 864 ± 14 | — | — | — | — | — |
| $K_{170}L_{30}$ | — | fl | 22 ± 3 | 183 ± 10 | 595 ± 9 | 1350 ± 55 | — | — | — |
| $K_{180}L_{20}$ | — | — | — | fl | fl | 27 ± 1 | 68 ± 1 | 136 ± 2 | — |
| $K_{190}L_{10}$ | — | — | — | — | — | — | — | fl | fl |
| $K_{200}$ | — | — | — | — | — | — | — | fl | fl |
| $R_{180}L_{20}$ | — | — | — | — | fl | 24 ± 1 | 76 ± 1 | 163 ± 1 | — |
| $E_{180}L_{20}$ | — | — | — | fl | 75 ± 2 | 217 ± 6 | 482 ± 4 | — | — |
| $K_{170}L_{30}$ In ACSF | — | — | — | — | — | 470 ± 11 | — | — | — |
| $K_{180}L_{20}$ In ACSF | — | — | — | — | — | 57 ± 3 | — | — | — |

Boxes = gels tested in vivo
Fl = fluid
— = not studied
SEQ ID Nos for the block copolypeptides are provided elsewhere herein.

2. Properties of DCH Injected into Forebrain

Figure 2:
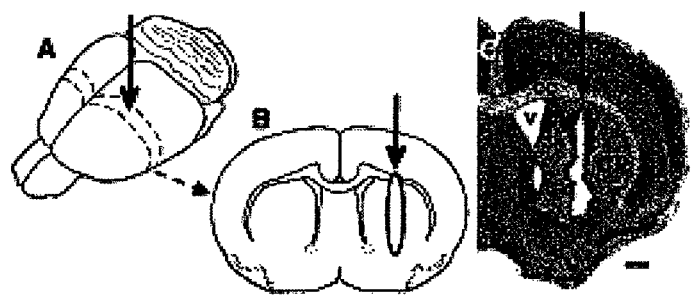
FIG. 2 shows stereotaxic injection of DCH in mouse forebrain.
Figure 3:
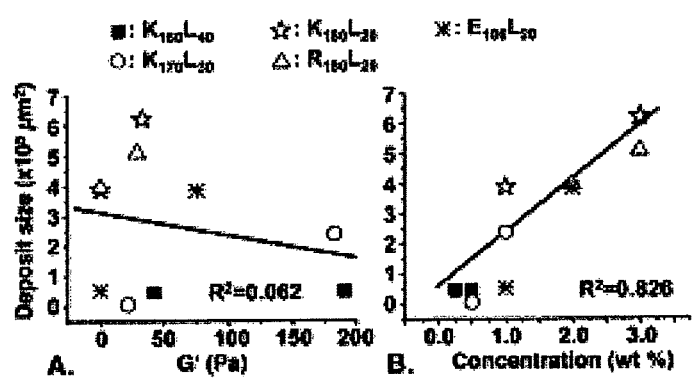
FIG. 3A is a graph showing no statistically significant correlation ($R^2$=0.062, p>0.05) between in vitro mechanical properties (G', Pa) and deposit size across different DCH formulations.
FIG. 3B is a graph showing a significant correlation ($R^2$=0.862, p<0.001) between concentration (wt/vol) and deposit size for different individual DCH formulations. Identical volumes (2 µl) were injected in all cases. The SEQ ID NOs are: $K_{160}L_{40}$ (SEQ ID NO:10), $K_{170}L_{30}$ (SEQ ID NO:9), $K_{180}L_{20}$ (SEQ ID NO:8), $R_{180}L_{20}$ (SEQ ID NO:26), $E_{180}L_{20}$ (SEQ ID NO:14).

To evaluate properties such as consistency and porosity, and to test the biocompatibility of DCH in vivo in CNS tissue, we injected 2 µl volumes into the mouse forebrain. Injections were made into the center of the caudate putamen nucleus (CPN), a large homogenous forebrain structure that is easily targeted (FIG. 2). The CPN contains a large population of neuronal cell bodies intermingled with bundles of myelinated axons that provides a good site to evaluate DCH integration with, and effects on, host CNS tissue, including degree of induction of gliosis and inflammation, potential toxicity towards neurons, myelin or axons and ability to act as a scaffold for growth and migration of host cells and nerve fibers, as discussed below.

Mice injected with DCH into the CPN exhibited no detectable adverse effects and were behaviorally indistinguishable from mice injected with an equivalent amount of physiological saline during routine monitoring over survival periods from 1 to 8 weeks after injection. We began our histological evaluations by comparing the in vitro physical properties of various DCH formulations (Table 3) with their properties after different times in vivo, such as: (i) ability to form deposits, (ii) consistency and porosity of deposits and (iii) appearance of deposits over time in vivo.

a. Deposit Formation by DCH In Vivo

We first evaluated the ability of DCH of various compositions and concentrations to reassemble into 3-dimensional gels and form deposits after injection in vivo. We examined a series of DCH designed to be injectable and with rheological properties similar to that of brain tissue. These DCH were similar in their total molecular chain length of ~200, but varied in (i) amino acid composition, (ii) ratio of hydrophilic to hydrophobic amino acids and (iii) concentration (Table 3). For comparison we also examined $K_{200}$ (SEQ ID NO:39) and $K_{190}L_{10}$ (SEQ ID NO:7), which had either no, or only a short, hydrophobic component and did not form gels in vitro even at very high concentrations (Table 3).

We compared in vivo properties of different DCH formulations in mouse forebrain. In this study, images of different DCH formulations at 1 week after injection of 2 µl into the CPN were examined in cresyl violet stained tissue sections. Detail images were generated using differential interference contrast (DIC) microscopy to reveal the microstructure of the DCH deposits.

One week after injection into the CPN, individual DCH formulations exhibited clear differences in their ability to reassemble into gels and form deposits with 3-dimensional structure in vivo. As expected, $K_{200}$ and $K_{190}L_{10}$, which were fluids in vitro, did not gel or form detectable deposits in vivo. When comparing different DCH formulations we found that gel strength in vitro (as determined by measuring G' values) did not consistently correlate with deposit formation in vivo. For example, $K_{180}L_{20}$-3%, $E_{180}L_{20}$-2% and $R_{180}L_{20}$-3% exhibited weak gel strength in vitro (Table 3), but consistently self-assembled into deposits with well-formed 3-dimensional structures in vivo. In contrast, $K_{170}L_{30}$-0.5% and $K_{160}L_{40}$-0.25%, which exhibited similar gel strengths in vitro, and $K_{160}L_{40}$-0.5%, which exhibited a much higher gel strength in vitro (Table 3), were all not able to self-assemble and form deposits with 3-dimensional structure in vivo. $K_{170}L_{30}$-1%, which exhibited a greater gel strength in vitro (Table 3), was able to self-assemble and form small uneven deposits in vivo.

We did find that for any given DCH formulation, increased sample concentration correlated both with increased gel strength in vitro (Table 3) and with increased deposit size in vivo as shown qualitatively for $K_{180}L_{20}$. Quantitative evaluation of deposit size confirmed these observations and showed that when comparisons were made among the different DCH formulations studied, there was no correlation between gel strength in vitro and deposit size in vivo. In contrast, for many different DCH samples, there was a consistent and significant correlation between the concentration of that DCH and its deposit size in vivo. The lack of correlation of gelation strength in vitro with deposit formation in vivo across different DCH formulations may be explained by the differential effect of ionic media on different DCH formulations. We have previously shown that the presence of salts increases the gel strength of DCH with high K to L ratios, but decreases the gel strength of DCH with low K to L ratios due to the decreased solubility of polylysine in ionic media compared to pure water (Nowak et al. (2003) (supra)). We confirmed this observation here, where 3%-$K_{180}L_{20}$ exhibited a higher G' value, but $K_{170}L_{30}$ had a lower G' value, in artificial cerebrospinal fluid as compared with water (Table 3).

b. Consistency, Density and Porosity of DCH Deposits In Vivo

To examine the consistency and porosity of DCH deposits in vivo we used differential interference contrast (DIC) microscopy of tissue sections containing DCH deposits that had been fixed in situ by cardiac perfusion with paraformaldehyde. Paraformaldehyde fixed deposits of $K_{180}L_{20}$-3%, $E_{180}L_{20}$-2% and $R_{180}L_{20}$-3% in forebrain sections all exhibited even consistencies with roughly similar degrees of porosity. Deposits of $K_{170}L_{30}$-1% appeared to have a higher density with less visible porosity. Comparison of $K_{180}L_{20}$ at different concentrations indicated that the consistency and porosity of deposits in vivo could be tuned by altering the DCH concentration, such that 1%-$K_{180}L_{20}$ exhibited a very porous and often discontinuous structure with large voids, 3%-$K_{180}L_{20}$ exhibited an even consistency with a porous microstructure in the cellular size range, and 5%-$K_{180}L_{20}$ exhibited an even, dense consistency with a less porous microstructure. Immunohistochemical staining of 3%-$K_{180}L_{20}$ with an antibody directed against poly-lysine revealed the network structure of condensed DCH fibrils that form the porous structure observed with DIC optics. Similar structures have been observed in previous studies using laser scanning confocal microscopy and cryogenic transmission electron microscopy in vitro (Nowak et al. (2002) (supra); Pochan et al. (2002) (supra)).

Figure 4:
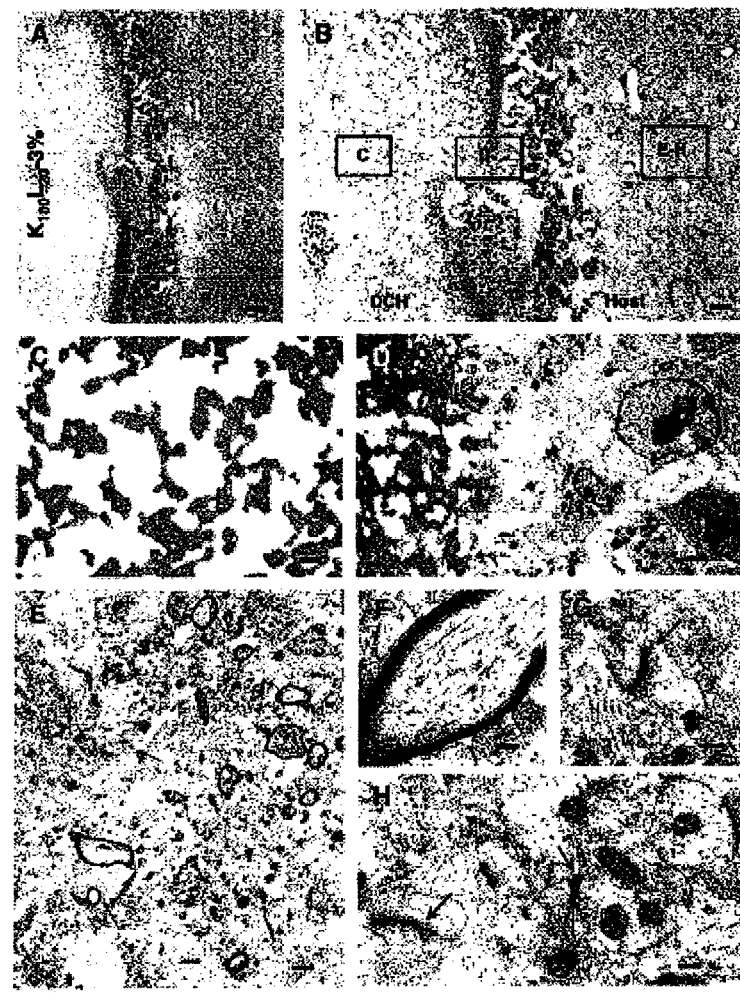
FIG. 4 shows an electron microscopic evaluation of DCH and neighboring brain tissue.

We next evaluated the ultrastructural appearance of DCH deposits and host tissue using electron microscopy after fixation with glutaraldehyde and paraformaldehyde. We investigated in particular 3%-$K_{180}L_{20}$ because of its desirable intermediate porosity noted at the light microscopic level. Examination of 3%-$K_{180}L_{20}$ deposits in semi-thin plastic sections (FIG. 4A,B) and at the electron microscopic level (FIG. 4C) after 1 week in vivo confirmed their even consistency and porous microstructure and clearly revealed the lattice-like network of DCH fibrils that interconnect to give the deposits their 3-dimensional structure. At the borders to host tissue, the DCH structure was denser with smaller pore sizes (FIG. 4B,D), but there was good integration of the DCH with host tissue, such that fibrils of DCH appeared intermingled with processes of host cells (FIG. 4D). The borders of DCH deposits were consistently surrounded by a thin rim of host reactive glial cells, which was generally in the range of several cell bodies (about 100 µm) thick (FIG. 4A,B,D). This rim of cells was evaluated in more detail using immunohistochemistry as described below. Immediately adjacent to the thin rim of reactive glial cells, and consistently within several hundred micrometers of the edge of the DCH deposit, the host neuropil had a normal ultrastructure (FIG. 4B,E), with normally appearing myelin and axons (FIG. 4F), normal dendritic spines and synapses (FIG. 4G,H) and normally appearing subcellular structures such as synaptic vesicles and mitochondria (FIG. 4G-H). Electron microscopic analysis also indicated that there was little or no diffusion of detectable $K_{180}L_{20}$ gel particles away from the deposit into the surrounding host neuropil for any appreciable distance beyond the 100 μm rim of reactive glial cells (FIG. 4D-H).

To evaluate further the potential diffusion of DCH particles into host tissue, we covalently conjugated the fluorescent probe, Texas Red (TR), to a 3%-$K_{180}L_{20}$ sample, and injected 2 μl into the CPN. Fluorescence microscopy of deposits of 3%-$K_{180}L_{20}$-TR after 1 week in vivo indicated that there was some diffusion of labeled DCH particles into host tissue within the first 100 μm adjacent to the deposit, but little or no diffusion of labeled DCH was routinely detectable beyond this distance.

c. Appearance of DCH Deposits Over Time In Vivo

We next monitored the appearance and properties of DCH deposits at the light and electron microscopic levels after 2, 4 and 8 weeks in vivo, focusing on 3%-$K_{180}L_{20}$. After 1 week in vivo, all 3%-$K_{80}L_{20}$ deposits exhibited essentially no detectable cells within the DCH deposit, and over time thereafter, there was a gradually progressive in-growth of host cells. At the light microscopic level, after two weeks in vivo, 3%-$K_{180}L_{20}$ deposits exhibited many diffusely scattered cells, which increased in density to many cells after 4 weeks, and to a packing density of cells similar to that of adjacent host tissue after 8 weeks. Electron microscopy at two weeks revealed that many cells and cellular processes were intermingled among DCH fibrils throughout the deposits and that there was substantive direct contact between cells and DCH fibrils in a manner suggesting that cells and processes were migrating along the fibrils). At 4 and 8 weeks, staining with cresyl violet indicated that deposits were packed with several different types of cells including glia and other non-neuronal cells. In agreement, electron microscopy demonstrated the presence within the 3%-$K_{180}L_{20}$ deposits after 4 or 8 weeks in vivo of cell nuclei with the ultrastructural characteristics (Peters et al. (1991) The fine structure of the nervous system, Third Edition. New York: Oxford University Press) of endothelia and different types of glia. Immunohistochemical evaluation of the type of cells migrating into the deposits is described below.

It is noteworthy that the gradual, time dependent in-growth of cells into 3%-$K_{180}L_{20}$ deposits appeared to occur in parallel with a gradual dissolution of DCH microstructure within the deposit as visible at both the light and electron microscopic levels. Whereas the lattice-like network of extracelluar DCH fibrils in deposits was clearly visible on ultrastructural analysis at both 1 and 2 weeks, electron microscopy also indicated that after 4 weeks in vivo there was a clear diminution in the amount of extracelluar DCH fibrils in the deposits as compared with 1 or 2 weeks. Moreover, after 8 weeks in vivo there were essentially no extracelluar DCH fibrils detectable by electron microscopy within the deposits and there appeared to be little or no extracelluar DCH, such that most or all of the DCH had either dissolved and/or been phagocytosed as suggested by the presence of many clear intracellular vacuoles. These changes of cell in-growth and dissolution of the DCH microstructure over time occurred with a small reduction in the overall size of deposits relative to the sizes observed at 1 week, however, the regions occupied by cells that had grown into the deposits remained clearly demarcated and easily detected after 4 or 8 weeks.

3. DCH Trigger Minimal Gliosis, Inflammation or Toxicity

Injuries or foreign materials in the CNS elicit reactive gliosis and inflammation, characterized by astrocyte reactivity, microglial reactivity and in severe cases by recruitment of blood borne inflammatory cells. To examine the responses elicited by DCH formulations we used immunohistochemistry for GFAP as a marker for reactive astrocytes, CD45 as a marker for microglia and blood borne inflammatory cells and CD3 as a marker for T cells. We compared the degree of astrogliosis and inflammation elicited by injection into the CPN of sterile physiological saline, a widely used vehicle for CNS injections, with that elicited by various DCH formulations.

a. Minimal Reactive Astrogliosis

The penetrating injury of inserting cannulae and injecting 2 μl of sterile physiological saline into the CPN consistently induced a moderately pronounced response of astrocyte reactivity with up-regulation of GFAP expression and hypertrophy of astrocytes when compared with uninjected tissue. In this study, images were taken of tissue sections through the CPN immunohistochemically stained for the reactive astrocyte marker, GFAP. This astrocyte reactivity was maximal at 1 week, extended for several hundred micrometers into host tissue adjacent to the cannula insertion sites, and had resolved considerably by 8 weeks. In all cases, the reactive astrogliosis was restricted to the immediate vicinity of the injection cannula and never extended beyond the borders of the CPN. Injections of 2 μl of the DCH, 3%-$K_{180}L_{20}$, also elicited a moderate reactive astrogliosis, which was no more severe than, and resolved as quickly as, the reaction associated with injections of physiological saline. At all time points examined after DCH injections, the rim of reactive and hypertrophic astrocytes in the host tissue along the borders of the deposit was of a similar size to that adjacent to injections of physiological saline. Astrocytes did not migrate into DCH deposits in substantive numbers, even after 8 weeks (see below). In all cases, the reactive astrogliosis was restricted to the immediate vicinity of the DCH deposits and never extended beyond the borders of the CPN. Similar observations were made with other DCH formulations, including 1%-$K_{180}L_{20}$, 5%-$K_{180}L_{20}$, 0.5%-$K_{170}L_{30}$, 1%-$K_{170}L_{30}$, 0.25%-$K_{160}L_{40}$, 0.5%-$K_{160}L_{40}$, 3%-$R_{180}L_{20}$, 5%-$R_{180}L_{20}$, 1%-$E_{180}L_{20}$ and 2%-$E_{180}L_{20}$, which all triggered levels of reactive gliosis similar to those just described for injections of physiological saline and 3%-$K_{180}L_{20}$.

b. Minimal Inflammatory Response or Immune Surveillance

Injection of 2 μl of sterile physiological saline into the CPN consistently induced a mild inflammatory response of activated CD45-positive microglia when compared with uninjected tissue. In this study, images were taken of tissue sections through the CPN immunohistochemically stained for the inflammatory and immune cell marker, CD45. This inflammatory response was maximal at 1 week, extended a few hundred micrometers into host tissue adjacent to the cannulae, and was largely resolved by 8 weeks. In addition to activated microglia, small numbers of globoid leukocytes were present in the immediate vicinity of the saline injection sites at all time points examined. In all cases, the inflammatory response was restricted to the immediate vicinity of the injection cannula and never extended beyond the borders of the CPN. Injections of 2 μl of the DCH, 3%-$K_{180}L_{20}$, elicited a mild inflammatory response, which was no more severe than, and resolved as quickly as, the response associated with injections of physiological saline. At all time points examined after DCH injections, the rim of CD45 positive activated microglia and the numbers of CD45 positive globoid leukocytes in the host tissue along the borders of DCH deposits were of a similar appearance and magnitude to those adjacent to injections of physiological saline. Similar observations were made in semithin sections or with electron microscopy. It is interesting to note that at 1 week after injections there were no CD45 positive cells inside deposits of 3%-$K_{180}L_{20}$, whereas by 8 weeks after injections, a number of CD45 positive cells had migrated into the deposits as described below. In all cases, the inflammatory response in host tissue was restricted to the immediate vicinity of the DCH deposits and never extended beyond the borders of the CPN.

To evaluate more specifically the nature of the globoid CD45 positive leukocytes observed in the vicinity of injections of either saline or DCH, we used immunohistochemistry for CD3 to detect T cells and to assess immune surveillance. In this study, images were taken of tissue sections through the CPN immunohistochemically stained for the T-cell marker, CD3. As expected, we found a small number of CD3 positive leukocytes in the immediate vicinity of the saline injections sites at all time points and that T cells continued to monitor the sites of cannula insertion and saline injection even after 8 weeks). We also found that an essentially equivalent numbers of CD3 positive leukocytes were present in the immediate vicinity of the DCH or saline injection sites at all time points and that an essentially equivalent density of T cells were present in DCH deposits after 8 weeks as were present 8 weeks after injection of saline. In all cases, the T cell response in host tissue was restricted to the immediate vicinity of the saline injections or DCH deposits and never extended beyond the borders of the CPN.

Similar observations were made with other DCH formulations, including 1%-$K_{180}L_{20}$, 5%-$K_{180}L_{20}$, 0.5%-$K_{170}L_{30}$, 1%-$K_{170}L_{30}$, 0.25%-$K_{160}L_0$, 0.5%-$K_{160}L_{40}$, 3%-$R_{180}L_{20}$, 5%-$R_{180}L_{20}$, 1%-$E_{180}L_{20}$ and 2%-$E_{180}L_{20}$, which all triggered levels of inflammation similar to those just described for injections of physiological saline and 3%-$K_{180}L_{20}$.

c. No Detectable Toxicity to Neurons, Myelin and Axons

The electron microscopic evaluation described above showed normally appearing host neuropil immediately adjacent to DCH deposits. To look further for any potential toxicity towards specific components of neural tissue we used immunohistochemistry for various markers to detect neurons and axons, and luxol fast blue staining to detect myelin. In this study, images were taken of tissue sections through the CPN immunohistochemically stained for the neural marker NeuN or stained with the myelin marker luxol fast blue (LFB). At all survival times examined, the density and appearance of (i) neurons stained for NeuN, (ii) myelinated axons stained with luxol fast blue or (iii) axons stained with two different markers (see below) was indistinguishable in the CPN tissue immediately adjacent to, and in direct contact with, injections sites of physiological saline or deposits of 3%-$K_{180}L_{20}$. In addition, no differences in the appearance or density of any of these markers were apparent in any part of the forebrains of mice injected either with saline or 3%-$K_{180}L_{20}$ at any time point examined. Similar observations were made with other DCH formulations, including 1%-$K_{180}L_{20}$, 5%-$K_{180}L_{20}$, 0.5%-$K_{170}L_{30}$, 1%-$K_{170}L_{30}$, 0.25%-$K_{160}L_{40}$, 0.5%-$K_{160}L_{40}$, 3%-$R_{180}L_{20}$, 5%-$R_{180}L_{20}$, 1%-$E_{180}L_{20}$ and 2%-$E_{150}L_{20}$, which all elicited no greater levels of toxicity to neurons, myelin or axons than those observed after injections of physiological saline.

4. Time Dependent Migration of Blood Vessels, Certain Glia and Some Nerve Fibers into DCH Deposits a. In-Growth of Endothelia and Glia As described above, observations made using cytological stains indicated a gradual migration of cells into deposits of 3%-$K_{180}L_{20}$ over time in vivo. To characterize the nature of this cellular in-growth, deposits of 3%-$K_{180}L_{20}$ were examined after 1, 2, 4 and 8 weeks in vivo using immunohistochemistry for the markers (i) PECAM, to identify vascular endothelial cells and blood vessels (Ilan et al. (2003) PECAM-1: old friend, new partners, *Curr Opin Cell Biol* 15, 515-524), (ii) NG2, to identify NG2-positive progenitors or polydendrocytes (Nishiyama (2007) Polydendrocytes: NG2 cells with many roles in development and repair of the CNS, *Neuroscientist* 13, 62-76), (iii) CD45, to identify microglia, and (iv) GFAP, to identify astrocytes (FIG. 14A-L). We also used electron microscopy to examine cellular ultrastructure.

After 1 week in vivo, in agreement with observations using cytological stains and electron microscopy, deposits of unmodified 3%-$K_{180}L_{20}$ exhibited no in-growth of cells positive for any of the immunohistochemical cellular markers, as shown for CD45 and GFAP. After 2 weeks in vivo, considerable in-growth of cells into 3%-$K_{180}L_{20}$ deposits was detected using cytological stains and electron microscopy in a manner suggesting migration of cells along fibrils (see above). Using immunohistochemistry, most of the cells detected within 3%-$K_{180}L_{20}$ deposits after 2 weeks in vivo appeared to be CD45 positive cells, with some PECAM-positive vascular endothelia, but no astrocytes or NG2-cells. After both 4 and 8 weeks in vivo, 3%-$K_{180}L_{20}$ deposits were packed with cells. Both immunohistochemical staining for PECAM and electron microscopy indicated that 3%-$K_{180}L_{20}$ deposits were well vascularized by 4 weeks and remained so after 8 weeks, and contained many well-formed blood vessels with normally appearing endothelial cells throughout the deposits. After 4 and 8 weeks, there were many NG2-positive cells scattered within the 3%-$K_{180}L_{20}$ deposits. After 4 and 8 weeks, many CD45 positive cells were evenly distributed throughout the 3%-$K_{180}L_{20}$ deposits and most of these had the appearance of stellate-shaped microglia that extended processes along blood vessels or among other cells. It is noteworthy that astrocytes, the other main glial cell type with migratory capacity, only migrated in small numbers into 3%-$K_{180}L_{20}$ deposits, even after 8 weeks in vivo. We found no NeuN positive neuronal cell bodies within DCH deposits. In agreement with the immunohistochemical observations, electron microscopy demonstrated the presence within the 3%-$K_{180}L_{20}$ deposits after 8 weeks in vivo of cell nuclei characteristic of endothelia, microglia and other glial cells such as astrocytes or NG2 cells.

In this context it is also interesting to note that a DCH prepared with the anionic amino acid, glutamate, 2%-$E_{180}L_{20}$, exhibited scattered cellular in growth already after 1 week in vivo, whereas DCH prepared with the cationic amino acids, lysine or homoarginine did not, and that cell in-growth into 2%-$E_{180}L_{20}$ was also markedly greater after 2 weeks in vivo.

b. Limited In-Growth of Nerve Fibers

To examine the effects of DCH deposits on local nerve fibers, and to look for evidence of nerve fiber in-growth into deposits, 3%-$K_{180}L_{20}$ deposits were examined after 1 to 8 weeks in vivo using immunohistochemistry for two different markers of nerve fibers, neurofilament M (NFM) and tyrosine hydroxlase (TH). NFM is a marker of large diameter axons present in fiber bundles that pass through the CPN, and TH is a marker for dopaminergic fibers abundant in the neuropil of the CPN. At all time points examined, there was no evidence of toxicity to either NFM or TH positive fibers in host tissue immediately adjacent to, and in direct contact with, 3%-$K_{180}L_{20}$ deposits. At all time points, the density of NFM or TH fibers in the CPN in immediate contact with DCH deposits was indistinguishable from that surrounding injection sites of saline. In addition, both NFM and TH fibers were found in small numbers to grow into DCH deposits with time. After 1 or 2 weeks in vivo, deposits of unmodified 3%-$K_{180}L_{20}$ exhibited no appreciable in-growth of nerve fibers positive for either NFM or TH. After 4 or 8 weeks in vivo, small numbers of single NFM-positive fibers were found crossing from the host into the deposits along the borders, and occasional NFM fibers were found within the center of deposits, generally in association with blood vessel walls. After 4 or 8 weeks in vivo, somewhat larger numbers of TH-positive fibers, often as bundles of fibers, were found crossing from the host into the deposits, particularly along the borders and sometimes penetrating well into the center of deposits, sometimes, but not always, in association with blood vessel walls.

D. Discussion

1. In vivo Mechanical Properties of DCH are Subtly Tunable

In the first part of this study, we showed that DCH are highly versatile and can easily be synthesized and dissolved in a wide variety of formulations that have rheological properties in the range of CNS tissue. We showed that DCH can be injected as liquids through small-bore cannulae and rapidly re-assemble into well-formed deposits in vivo, allowing facile and minimally invasive in vivo delivery. In addition, we showed that the size and physical properties (density/porosity) of DCH deposits in vivo can be varied subtly and predictably by small alterations in DCH composition or concentration. For example, both the gelation strength in vitro, and the size and porosity of deposits in vivo, could be varied in a predictable manner by altering either the (i) amino acids used in the hydrophilic copolymer chains, (ii) ratio of charged to hydrophobic amino acid residues, or (iii) concentration of DCH formulations. We tested a variety of DCH formulations that exhibited different in vitro properties and found that DCH of lysine and leucine ($K_mL_n$, where m and n are the numbers of lysine and leucine residues, respectively) formed in vivo deposits with desirable properties. We selected $K_mL_n$ DCH for detailed analyses because polylysine is routinely used as a substrate for neural cell cultures (Yavin et al. (1974) (supra); Svendsen et al. (1994) (supra); Sanjana et al. (2004) (supra)) and is a good candidate to interact well with neural tissue in vivo. We identified the DCH formulation of $K_{180}L_{20}$ as exhibiting good deposit formation with desirable properties that could be varied subtly according to weight percent concentration to achieve different degrees of deposit consistency and porosity that may be suitable for different applications.

2. DCH are Biocompatible, Nontoxic and Degrade Over Time in vivo

In the second part of this study, we tested the bio compatibility of DCH by examining the response of host CNS tissue to DCH deposits after various times in vivo. We compared the response to DCH with that to injection of sterile physiological saline, which is widely used as a vehicle for delivery of molecules into CNS parenchyma. Using a combination of routine histology, immunohistochemistry and electron microscopy, we found that DCH deposits elicited no more gliosis, inflammation, or toxicity to neurons, myelin or axons in the host tissue immediately adjacent to the deposits than did injections of physiological saline at all time points examined after 1 to 8 weeks in vivo. We also found that many host cells and some nerve fibers migrated into DCH deposits over time in vivo. Detailed analysis showed that the gliosis and inflammation around DCH deposits resolved at the same rate and to the same degree as observed after injection of saline, indicating that the DCH deposits were not eliciting any additional or prolonged gliosis or inflammatory response greater than that expected simply from the invasive injection procedure. In addition, over periods of up to two months of observation, all mice injected with DCH into the forebrain were indistinguishable in health and behavior from mice injected with physiological saline. DCH are composed of chains of naturally occurring amino acids linked by conventional peptide bonds and would be expected to degrade over time in vivo. Our electron microscopic findings confirmed this expectation and showed that (i) after 1 week in vivo, deposits of 3%-$K_{180}L_{20}$ consisted entirely of dense networks extracellular DCH fibrils, (ii) the density of extracellular fibrils decreased after 2 and 4 weeks as cellular in-growth increased, and (iii) by 8 weeks there were no detectable extracellular DCH fibrils, but there were many cells with clear vacuoles, suggesting that the DCH had either dissolved away or been phagocytosed. Nevertheless, although the DCH fibrils had degraded by 8 weeks in vivo, their remained behind a clearly identifiable formation of cells that had migrated into the deposits over time. Thus, taken together our findings show that deposits of DCH caused no detectable toxicity or adverse tissue response, and were degraded and cleared over time in vivo.

3. DCH Integrate Well with Host Cells and Nerve Fibers in vivo

In the third part of this study, we examined direct interactions between DCH deposits and host tissue and cells, focusing on 3%-$K_{180}L_{20}$, which as described above, exhibited a variety of desirable characteristics for biomaterial applications in the CNS. Electron microscopic evaluations over 1 to 8 weeks in vivo showed good integration of DCH microstructure with host cells at the borders of the deposits, such that there was a smooth transition from host tissue to the DCH fibrils that formed the scaffold of the deposit. Electron microscopy, routine light microscopy and immunohistochemistry all showed a gradual migration of host endothelia and glia into the DCH deposits between 2 and 4 weeks in vivo. By 4 weeks in vivo, deposits of 3%-$K_{180}L_{20}$ were densely vascularized with well-formed blood vessels and normally appearing endothelia. By 8 weeks in vivo, the deposits exhibited a cell density approximately similar to that of neighboring host tissue and contained three different types of host glial cells, including many finely branched microglia, some astrocytes and considerable numbers of NG2 cells, which are regarded as progenitor cells that can give rise to myelinating oligodendrocytes in the adult CNS (Nishiyama (2007) (supra)). The migration of such progenitors into DCH deposits suggests that DCH scaffolds can attract and support new cell growth in the CNS. In addition, considerable numbers of nerve fibers had grown into 3%-$K_{180}L_{20}$ deposits after 8 weeks. These observations suggests that DCH have potential for use as scaffolds to promote cell and axon growth in the CNS. This capacity may be enhanced by functionalizing the DCH through attachment of specific molecular epitopes that are able to provide matrix support with specific permissive or inhibitory migration guidance cues, of which many have been identified and some tested in combination with biomaterials in the CNS (Schmidt et al. (2003) Neural tissue engineering: strategies for repair and regeneration, *Annu Rev Biomed Eng* 5, 293-347; Zhang et al. (2005) Tissue-engineering approaches for axonal guidance, *Brain Res Brain Res Rev* 49, 48-64, 2005; Zhong et al. 2008) Biomaterials for the central nervous system, *J R Soc Interface* 5, 957-975). In this context it is also interesting to note that a different DCH formulation prepared with the amino acid glutamate, 2%-$E_{180}L_{20}$, exhibited considerable cell in-growth already after 1 week in vivo and was much more densely packed with cells after two weeks as compared with 3%-$K_{180}L_{20}$. These findings suggest that altering the amino acid composition of DCH may also represent a means of altering scaffold properties to regulate and manipulate cell or nerve fiber in-growth for specific applications. Taken together, our findings suggest that deposits of DCH have promise as scaffolds after injection into the CNS, which are able to support cell and nerve fiber in-growth and migration, and are biodegradable over time, but have the potential to leave behind a long-lasting, new cellular structure.

4. DCH can be Used for CNS Applications

A number of structural and functional features are likely to be required of materials for CNS applications including: non-toxicity; biocompatability; degradability; injectability; tunable mechanical properties (e.g. rigidity and porosity); ability to interact with cells; tunable sustained release of diffusible biologically active agents; and tunable presentation of extra-cellular matrix cues to support and guide cell migration or nerve fiber growth. Materials currently investigated for CNS applications have shown promise but also limitations. Materials prepared from natural polymers, e.g. hyaluronic acid (HA) (Hou et al. (2005) The repair of brain lesion by implantation of hyaluronic acid hydrogels modified with Laminin, *J Neurosci Methods* 148, 60-70), agarose (Stokols et al. (2006) Templated agarose scaffolds support linear axonal regeneration, *Tissue Eng* 12, 2777-2787), and fibrin (Taylor et al. (2006) Delivery of neurotrophin-3 from fibrin enhances neuronal fiber sprouting after spinal cord injury, *J Control Release* 113, 226-235), may possess desired biological signaling capability but may lack optimal mechanical properties (e.g. rigidity) and are not easily tuneable in this regard (Peppas et al. (2000) (supra); Lee et al. (2001) Hydrogels for tissue engineering, *Chem Rev* 101, 1869-1879)). Materials prepared from natural sources can also exhibit batch-to-batch variation and may be problematic due to immunogenicity and potential transmission of pathogens (Peppas et al. (2000) (supra); Lee et al. (2001) (supra)). A variety of synthetic or semi-synthetic materials are currently under investigation for CNS applications, including polymeric scaffolds based on cross-linked polyethyelene glycol (PEG) and polylysine (Ford et al. (2006) A macroporous hydrogel for the coculture of neural progenitor and endothelial cells to form functional vascular networks in vivo, *Proc Natl Acad Sci USA* 103, 2512-2517) HA either crosslinked with polylysine (Tian et al. (2005) Hyaluronic acid-poly-D-lysine-based three-dimensional hydrogel for traumatic brain injury, *Tissue Eng* 11, 513-525) or mixed with methyl cellulose (Gupta et al. (2006) Fast-gelling injectable blend of hyaluronan and methylcellulose for intrathecal, localized delivery to the injured spinal cord, *Biomaterials* 27, 2370-2379), agarose containing multilamellar lipid microtubules for sustained release (Jain et al. (2006) In situ gelling hydrogels for conformal repair of spinal cord defects, and local delivery of BDNF after spinal cord injury, *Biomaterials* 27, 497-504), and amphiphilic peptides (Holmes et al. (2000) Extensive neurite outgrowth and active synapse formation on self-assembling peptide scaffolds, *Proc Natl Acad Sci USA* 97, 6728-6733) or peptide amphiphiles that gel in salt solutions (Jain et al. (2006) (supra)). Some of these are non-injectable rigid materials that present impenetrable surfaces and are able to support cell and nerve fiber migration in vivo, but require substantial tissue disruption to achieve implantation of preformed scaffolds (Tian et al. (2005) (supra); Ford et al. (2006) (supra); Stokols et al. (2006) (supra); Taylor et al. (2006) (supra)). Others, such as the hyaluronan/methylcellulose (HAMC) mixtures (Gupta et al. (2006) (supra) and peptide amphiphile hydrogels (Jain et al. (2006) (supra)) are being tested as injectable, fast gelling scaffolds.

DCH compare favorably with these other materials and exhibit many characteristics desirable for CNS applications. DCH shear thin to liquids during injection and rapidly re-assemble into well-formed deposits that persist in vivo for prolonged periods of time. DCH are biocompatible, and integrate well with host cells and tissue. The time-dependent in-growth of certain cell types into DCH deposits suggests the potential for DCH deposits to serve as scaffolds for cell migration in the CNS in a cell or nerve fiber specific manner if they are functionalized with the appropriate migration guidance cues. DCH scaffolds may also have the potential to support grafted cells. The amino acid side-chains of DCH provide the potential for functionalization of DCH with a vast array of bioactive molecules, thus providing DCH with the potential for wide biological versatility, for example to serve as depots for sustained molecular release or to present covalently bound matrix molecules to support and guide cell migration. DCH can readily be labeled with probes to mark their location in vivo, as shown here with the fluorescent probe Texas Red, and which could be done using markers available for in vivo imaging. In addition, the synthesis of DCH can be modified readily and predictably to achieve subtly different mechanical properties, while retaining basic attributes. This important feature enables the in vivo properties of DCH to be fine-tuned in a context specific manner as might be required by different applications in the CNS. For example, different mechanical properties may be required for providing depot delivery with sustained release of diffusible molecules, as compared with providing a scaffold to bridge cell and nerve fiber migration across scar tissue or to fill wound cavities. In some cases, attributes of sustained release and scaffold may be required together. Fine-tuning of mechanical properties may also be important to achieve optimal integration of materials with host CNS tissues that have subtly different properties, for example after different insults such as traumatic or ischemic injury, or degenerative disease. Mechanical properties of extracellular surroundings can markedly, and differentially, influence growth properties of specific neural and glial cell types (Discher et al. (2005) (supra); Georges et al. (2006) (supra)). The ability to fine-tune the mechanical properties of DCH in subtle ways while retaining their basic attributes of tissue compatibility and their functional delivery capabilities makes them attractive sources candidates for therapeutic applications in the CNS. These properties can be readily optimized, using routine procedures. The properties of most other synthetic materials being investigated for CNS applications are not so easily tuned. Taken together, our findings show that DCH represent a new class of synthetic biomaterials with potential for CNS applications, and are good candidates for development of versatile and finely tunable vehicles for site-specific delivery as depots or scaffolds in the CNS.

Example II

Amphiphilic Diblock Copolypeptide Hydrogens as Therapeutic Depots

A. Introduction

We showed in Example I that DCHs exhibit little or no detectable in vivo toxicity and integrate well with host cells and nerve fibers in the forebrain. These attributes, together with the functionality of DCH, amino acid side chains, which allow conjugation of molecules to DCH indicate that DCHs are good candidates for development of therapeutic depots in the CNS. To obtain physiologically active matrices for certain applications, it is necessary to release the incorporated therapeutics (e.g. nucleic acids, oligopeptides, proteins, enzymes, carbohydrates, viruses, cells, etc.) in a controlled fashion. Ideally, this release occurs over an extended time to reduce the need for additional administrations of the therapeutics. Moreover, site-specific delivery via a hydrogel confines therapeutic activity to a precise location in the proximity of the injection site that can reduce potential side effects. The design of systems for controlled release of biomolecules presents several challenges, primarily related to the specific chemical structures of the drug substances and the unique properties of the matrices used for each application (Veronese et al. (1999) *Bioconjugation in pharmaceutical chemistry, Farmaco* 54, 497-516; Tessmar et al. (2007) Matrices and scaffolds for protein delivery in tissue engineering, *Adv Drug Deliv Rev* 59, 274-291).

In the last few years investigations carried out in several laboratories and using different experimental models have shown that chondroitinase ABC (chABC) digestion of chondroitin sulfate proteoglycans (CSPGs) in the CNS extracellular matrix enhances axonal plasticity, and improves the behavioral outcome after an injury. See, e.g., Galtrey et al. (2007) Promoting plasticity in the spinal cord with chondroitinase improves functional recovery after peripheral nerve repair, *Brain* 130, 926-939; Garcia-Alias et al. (2008) Therapeutic time window for the application of chondroitinase ABC after spinal cord injury, *Exp Neurol* 210, 331-338; Lin et al. (2008) ABC has a long-lasting effect on chondroitin sulfate glycosaminoglycan content in the injured rat brain, *J Neurochem* 104, 400-408). These encouraging results suggeset that the chABC can be used as a therapeutic drug for patients with damage to the CNS (Kwok et al. (2008) Proteoglycans in the central nervous system: plasticity, regeneration and their stimulation with chondroitinase ABC, *Restor Neurol Neurosci* 26, 131-145). In this Example, chondroitinase ABC was used as the model drug substance to demonstrate the capability of DCH as a therapeutic depot. Different release strategies are shown, and in vivo experiments and chemical synthesis were conducted.

B. Strategies for Release

1. Direct Loading (Silva et al. (2009) Growth Factor Delivery Approaches in Hydrogels, *Biomacromolecules* 10, 9-18)

The easiest way to add proteins and peptides to a hydrogel is their physical mixture into the gel matrix. However, if proteins are incorporated into materials that are not fully hydrated, without any further modification, typical release profiles show a rapid burst release during the initial swelling phase, eventually followed by the extended release of a certain amount of protein that was entrapped by the gel network. In fact, a controlled release of protein over a long time will not be expected from hydrogels since the rate of protein release is generally diffusion-controlled through aqueous channels within the hydrogels (Tabata et al. (2000) The importance of drug delivery systems in tissue engineering, *Pharm Sci Technol Today* 3, 80-89).

2. Covalent Binding

As an alternative to physical mixing, proteins or peptides can also be covalently attached to polymers through a cleavable linkage and then released afterwards when the linkage is cleaved. This covalent attachment can be achieved by reacting the different side chain functionalities of polymers with the amino acids of the proteins or peptides (e.g. aspartic acid, glutamic acid, lysine, arginine, cysteine, histidine, tyrosine, methionine, and tryptophan). This covalent attachment creates a stable product with good retention of the native protein state and activity. Ideally, any derivatization should result in a protein that performs exactly as it would in its unmodified form, but with the added functionality imparted by whatever is conjugated to it (Hermanson, *Bioconjugate Techniques*, Academic Press, Inc., 2008).

3. Amine Coupling

Figure 5:
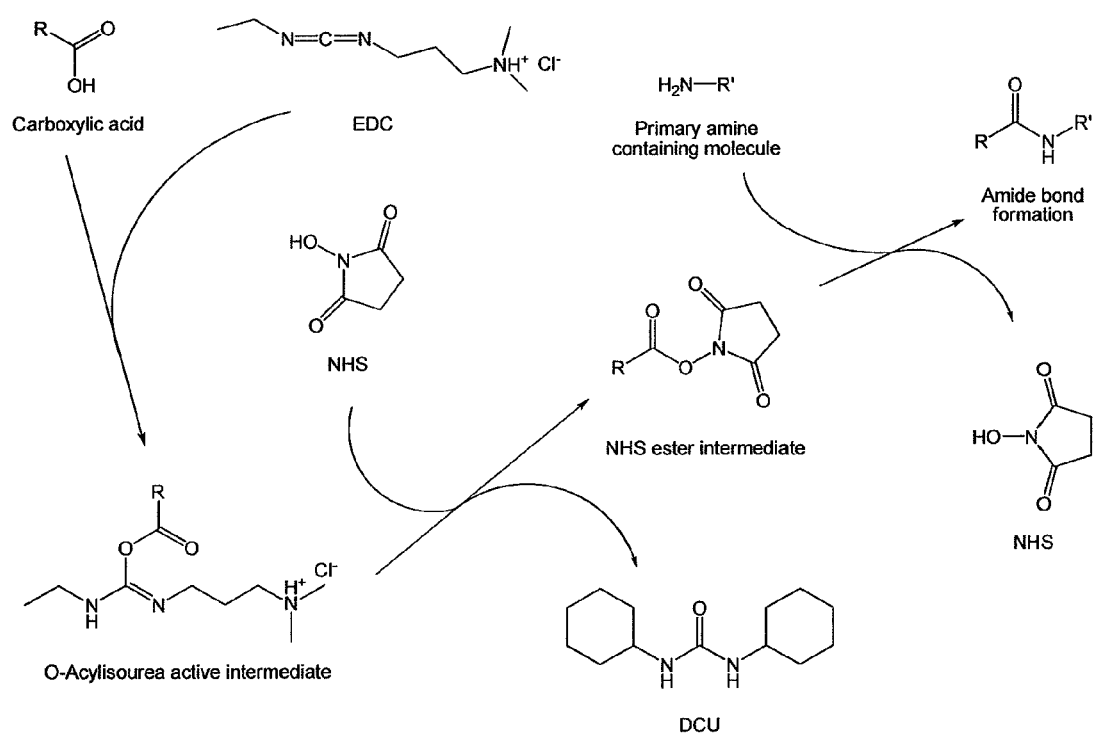
FIG. 5 shows amine coupling between a carboxylic acid and an amine to form an amide bond. EDC reacts with carboxylic acids to create an active-ester intermediate. The efficiency of an EDC-mediated reaction may be increased through the formation of a NHS ester intermediate.

The most common functional groups present in cross-linking or coupling reagents are groups that are able to react with amine-containing molecules. An amine-coupling process can be used to conjugate with nearly all protein or peptide molecules as well as a host of other macromolecules. Most of these reactions are rapid and occur in high yield to give stable amide or secondary amine bonds (Hermanson (2008) (supra)). Carboxylate groups activated as N-hydroxysuccinimide (NHS) esters are highly reactive toward amine nucleophiles. NHS ester-containing molecules that react with primary or secondary amines release the NHS leaving group and form stable amide and imide linkages. Using the water-soluble carbodiimide EDC, 1-ethyl-3-(3-dimethylaminopropyl) carbodiimide hydrochloride, a carboxylate-containing molecule can be transformed into an active ester functional group by reaction in the presence of NHS (FIG. 5). A peptide or protein can thus be conjugated through its carboxylate or amine groups to complimentary groups on either lysine or glutamate based DCHs using amine coupling.

4. Thiol-ene Click Chemistry

Sharpless and colleagues recently (Kolb et al. (2001) Click chemistry: Diverse chemical function from a few good reactions, *Angewandte Chemie-International Edition* 40, 2004) introduced a general concept of click chemistry, which is often exemplified as the copper-catalyzed Huisgen 1,3-dipolar cycloaddition of azides and alkynes (Binder et al. (2007) 'Click' chemistry in polymer and materials science, *Macromolecular Rapid Communications* 28, 15-54). According to its original definition, a click reaction must be modular, be wide in scope, give very high yields of product, generate only inoffensive byproducts, and be stereospecific (but not necessarily enantioselective). Processes must therefore have a high thermodynamic driving force. One reaction that is emerging as an attractive click process is the addition of thiols to alkenes (Posner (1905) Information on unsaturated compounds II The addition of mercaptan to unsaturated hydrocarbon. *Berichte Der Deutschen Chemischen Gesellschaft* 38, 646-657), which is currently called thiol-ene coupling (TEC) (Gress et al. (2007) Thio-click modification of poly [2-(3-butenyl)-2-oxazoline], *Macromolecules* 40, 7928-7933; Killops et al. (2008) Robust, Efficient, and Orthogonal Synthesis of Dendrimers via Thiol-ene Click Chemistry, *Journal of the American Chemical Society* 130, 5062-5064; Campos et al. (2008) Development of thermal and photochemical strategies for thiol-ene click polymer functionalization, *Macromolecules* 41, 7063-7070; Pascal et al. (2008) Photochemical Surface Patterning by the Thiol-Ene Reaction. *Angewandte Chemie International Edition* 47, 4421-4424; ten Brummelhuis et al. (2008) Thiol-Ene Modification of 1,2-Polybutadiene Using UV Light or Sunlight, *Macromolecules* 41, 9946-9947; Alessandro Dondoni (2008) The Emergence of Thiol-Ene Coupling as a Click Process for Materials and Bioorganic Chemistry, *Angewandte Chemie International Edition* 47, 8995-8997).

The photochemically/thermally-induced version of this reaction is known to proceed by a radical mechanism to give an anti-Markovnikov-type thioether. The click status of this reaction is supported by it being highly efficient and orthogonal to a wide range of functional groups, as well as for being compatible with water and oxygen. Conducting the thiol-ene reactions under benign reaction conditions and without the use of any metal catalysts allows for an environmentally friendly process to be developed, further enhancing the attractive nature of this process. In this Example, we develop a universal bioconjugation protocol based on thiol-ene click chemistry.

5. Alkene-functionalization of DCHs

Alkene groups can be linked to the functional groups of hydrophilic side chains in DCHs via different approaches. These include a permanent or cleavable linkage to the NCA monomer or to the DCH polymer.

6. Permanent or Cleavable Linkage

Small amounts of therapeutics can be released over sustained periods of days and even months in polymeric controlled-release systems. The desired release profile can be controlled by using a suitable cleavable linkage that would respond to different stimuli such as pH, temperature, or other molecules. In this study, we used a cleavable crosslinker, 4-allyloxy-4-oxo-butanoic acid for the initial trial. It has an alkene group on one end that can be used for thiol-ene coupling to thiolated proteins. Its other end is a carboxylic group that can be coupled to the $N_\epsilon$-amine on the side chain of lysine in DCH. There is an ester group in the middle of the linker that should hydrolyze slowly over time under physiological conditions.

7. Alkene-functionalized NCA Monomer

Figure 6:
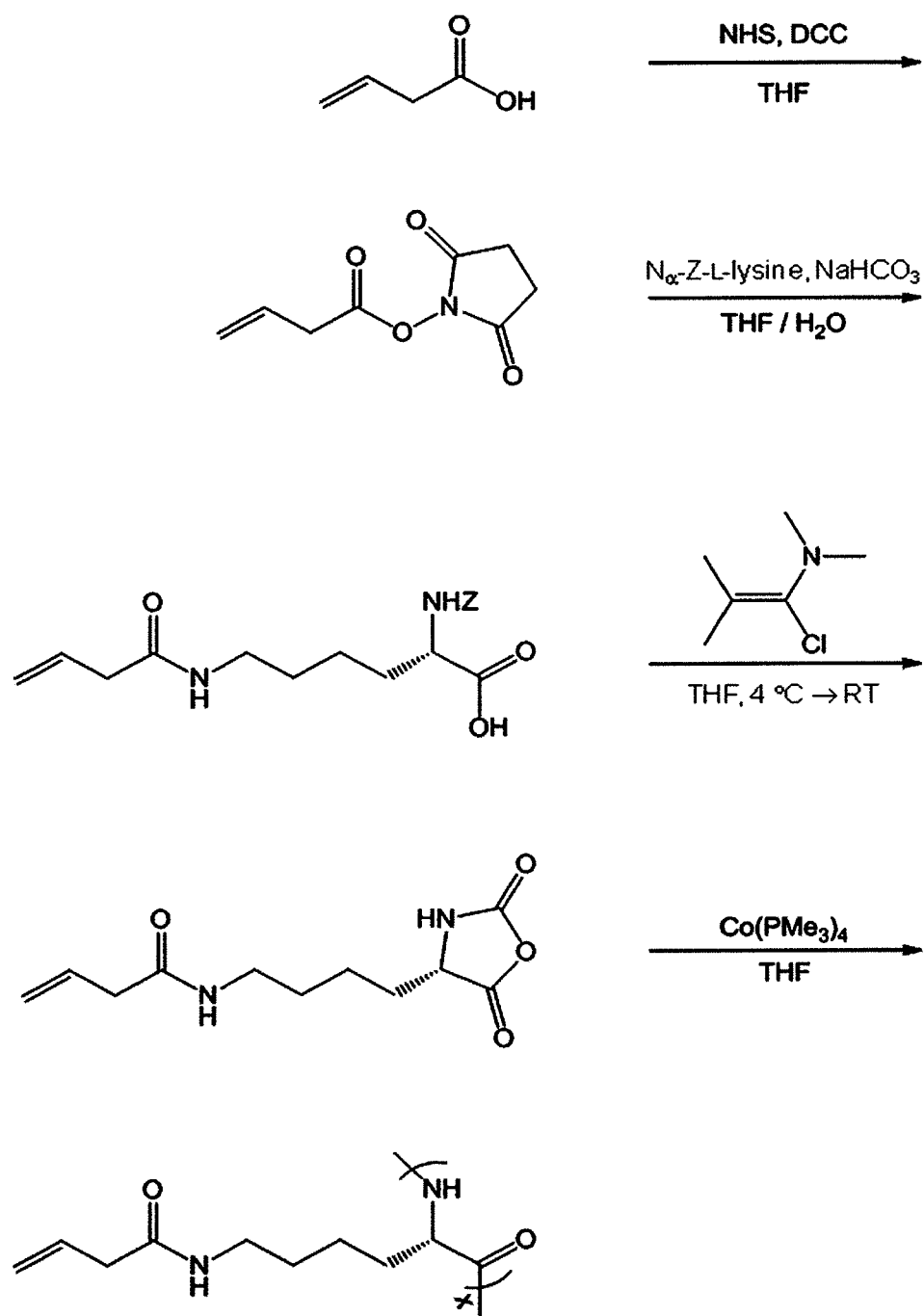
FIG. 6 shows the synthesis of alkeneene-functionalized poly-L-lysine in DCH from alkene-functionalized NCA monomers. An alkenene-functionalized lysine NCA monomer can be synthesized first and then polymerized with a cobalt initiator to form an alkene-functionalized poly-L-lysine segment.

As shown in FIG. 6, 3-butenoic acid can be conjugated to the $N_\epsilon$-amine in $N_\alpha$—Z-lysine via amine coupling and then cyclized to form the NCA monomer with (1-chloro-2-dimethylamino-2-methyl) propene. The alkene-functionalized NCA monomer can then be copolymerized using $Co(PMe_3)_4$ to obtain alkene-functionalized DCH polymers.

8. Alkene-functionalized DCH Polymer

Figure 7:
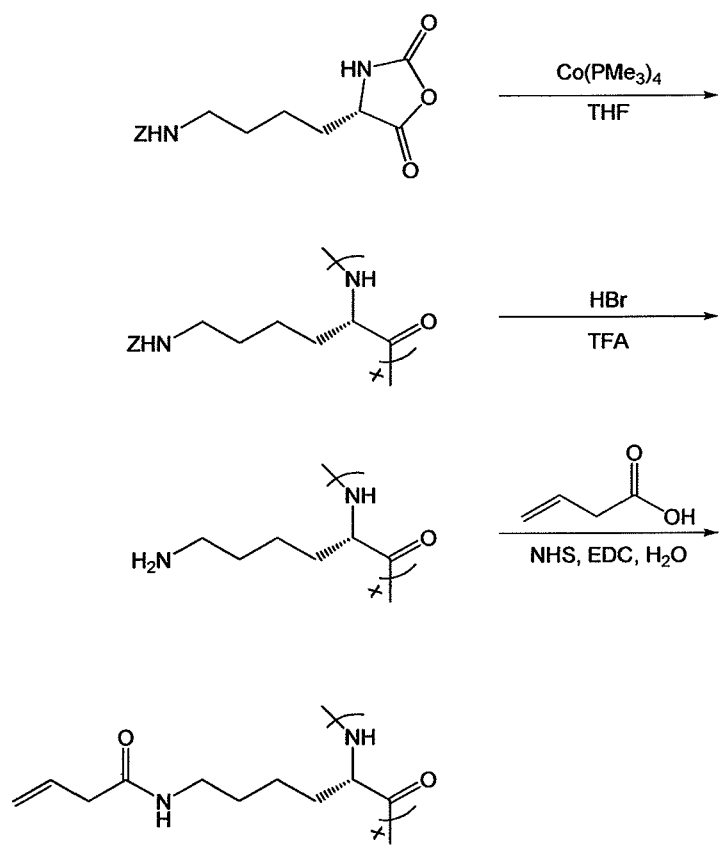
FIG. 7 shows the synthesis of alkene-functionalized poly-L-lysine by conjugating 3-butenoic acid to poly-L-lysine. Poly-L-lysine in DCH can be synthesized first and 3-butenoic acid can then be conjugated to the free $N_\epsilon$-amines via amine coupling.
Figure 8:
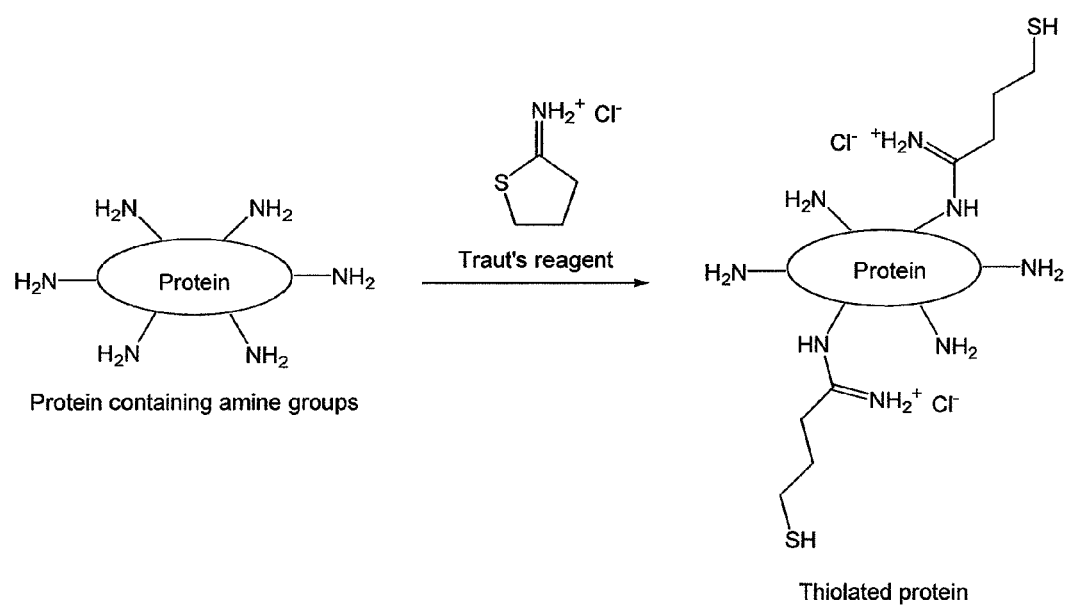
FIG. 8 shows thiolation of a protein using Traut's reagent. Reaction of an amine containing protein with Traut's reagent to generate a thiol-functionalized protein.

As shown in FIG. 7, 3-butenoic acid can be attached to $N_\epsilon$-amine in the poly-L-lysine segments of DCH via amine coupling.

9. Thiolation of Proteins Using Traut's Reagent

Large proteins often contain more than one polypeptide chain and these multi-subunit proteins have complex structures. Subunits may be held together by noncovalent contacts, such as hydrophobic or ionic interactions, or by covalent disulfide bonds formed by a cysteine residue of one polypeptide chain being cross-linked to a cysteine sulfhydryl of another chain. Not surprisingly, chemical modification of amino acid constituents of a protein may also cause significant disruption of its overall 3D structure. It is then often desirable to introduce additional functional groups onto proteins for conjugation. Traut's reagent, 2-iminothiolane, is a cyclic imidothioester that can react with primary amines in a ring-opening reaction that generates a free sulfhydryl without breaking the native disulfide linkages inside a protein. The newly generated free sulfhydryl can be conjugated to the alkene groups on the side chains of DCHs via the thiol-ene reaction.

10. Thiol-ene Coupling to Side Chain-functionalized DCHs

Figure 9:
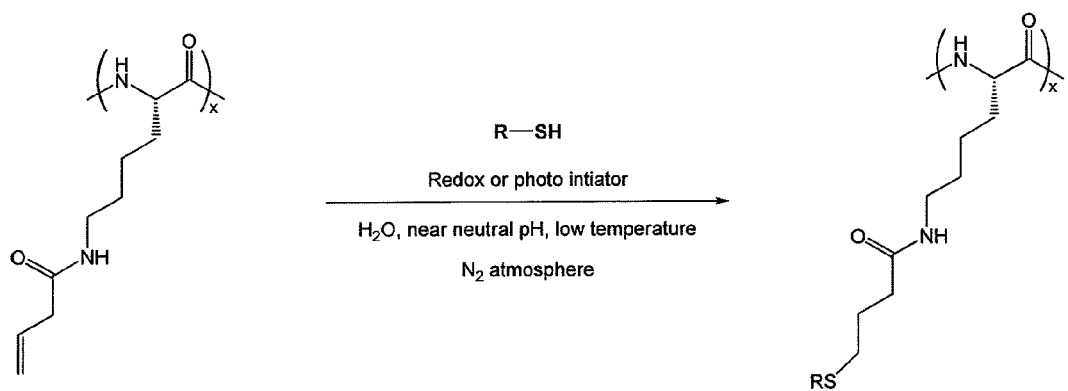
FIG. 9 shows thiol-ene coupling of thiolated protein to alkene-functionalized lysines in DCH. Ideally, this bioconjugation should occur in water at physiological pH and low temperature (4° C. to room temperature) in a reasonable reaction time period. Because thiol-ene coupling is a radical addition of a sulfur radical to an alkene group, approaches that can generate free radicals at low temperature may be applied to obtain reaction conditions for bioconjugation. Suitable approaches include redox or photochemical initiation.
Figure 9:
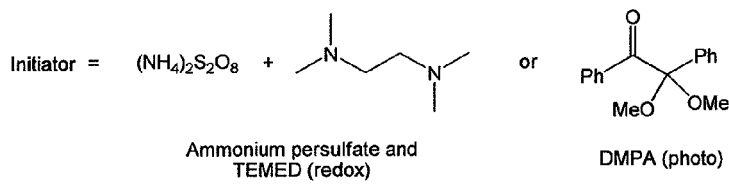

Thiol-ene coupling is a sulfur radical addition to an alkene group to form a thioether bond. Ideally, for its potential application in bioconjugation, the reaction is easily carried out in an aqueous environment at physiological pH and low temperature (about 4° C. to room temperature) in a reasonable reaction time period. Even though thiol-ene coupling has been known for many years, reaction conditions suitable for the bioconjugation of proteins had not been well established prior to the present application. In the past, most reported TEC reactions were carried out in organic solvents with strong UV light at high temperature in time periods of days and even months (Gress et al. (2007) (supra); Killops et al. (2008) (supra); Campos et al. (2008) (supra); Pascal et al. (2008) (supra); ten Brummelhuis et al. (2008) (supra); Sven Wittrock et al. (2007) Synthetic Vaccines of Tumor-Associated Glycopeptide Antigens by Immune-Compatible Thioether Linkage to Bovine Serum Albumin, *Angewandte Chemie International Edition* 46, 5226-5230). Because TEC involves a radical addition, approaches that can initiate radical generation at low temperature are more suitable to obtain the ultimate reaction conditions suitable for bioconjugation (FIG. 9).

C. Methods

1. Synthesis of DCH was Performed as Described Above.
2. Direct Loading of chABC with $K_{180}L_{20}$ $K_{180}L_{20}$ powder was dissolved in physiological saline at the concentration of 6%. ChABC was reconstituted in physiological saline at a concentration of 100 U/mL. 50 μL of chABC solution was added to 50 μL of $K_{180}L_{20}$ gel under gently stirring. The final gel contains 3%-$K_{180}L_{20}$ and 50 U/mL of chABC.

3. Covalent Binding a. ChABC Conjugated to $K_{180}L_{20}$ Via Amine Coupling

A chABC and $K_{180}L_{20}$ mixture was prepared as described above. 10 equiv. of NHS and 10 equiv. of EDC were then added to the mixture with stirring for 24 hours. The mixture was used directly.

b. Thiol-Ene Click Reaction

Synthesis of hydrolysable linker, 4-allyloxy-4-oxo-butanoic acid (Casimir et al. (1995) First Application of the Dakin-West Reaction to Fmoc Chemistry—Synthesis of the ketomethylene tripeptide fmoc-Nα-Asp(tBu)-(R,S Tyr(tBu)Ψ(CO—CH$_2$)Gly-OH. *Tetrahedron Letters* 36, 4797-4800; Catry et al. (2007) Synthesis of functionalised nucleosides for incorporation into nucleic acid-based serine protease mimics, *Molecules* 12, 114-129)

To a solution of succinic anhydride (2.0 g, 2.0 mmol) in toluene (45 mL) was added 4-dimethylaminopyridine (100 mg). Allyl alcohol (1.5 mL, 2.2 mmol) was added dropwise and the reaction mixture was refluxed for 5 hours. The solid impurities were filtered and the clear filtrate was collected. The solvent was removed under reduced pressure and the residue was purified by bulb-to-bulb distillation (0.04 mm Hg, 140° C.) to obtain colorless oil (yield 90%, b.p. 108° C./0.15 mbar). $^1$H-NMR (300 MHz, CDCl$_3$, δ ppm): 2.65, 4.58, 5.30, 5.89, 11. IR (ν cm$^{-1}$ THF): 3090, 2940, 1737, 1650, 1415, 1346, 1170, 992, 936, 842, 558.

Alkene-Functionalized Monomer

Synthesis of NHS-ester of 3-butenoic acid

NHS ester of 3-butenoic acid was synthesized based following literature procedure.[32] 3-butenoic acid (1.0 g, 1.2 mmol) and NHS (1.47 g, 1.28 mmol) were dissolved in THF (30 ml). The solution was cooled in an ice bath and N,N'-dicyclohyxylcarbodiimide (DCC, 2.4 g, 1.2 mmol) was added under stirring. A white precipitate, dicyclohexylurea (DCU), formed after ~5 min and the mixture was stirred for 1 hour at 0° C. The reaction proceeded at 4° C. overnight without any agitation. DCU was then removed by filtration. The filtrate was concentrated to give a viscous oil containing some residual DCU. The crude product was re-dissolved in a small volume of THF and then filtered. This procedure was repeated until a clear THF solution was obtained. The solvent was removed and the product was then washed with hexane. Residual solvents were removed under vacuum until a constant weight was obtained. $^1$H-NMR (500 MHz, CDCl$_3$, δ ppm): 2.64, 2.90, 5.21, 5.24, 5.94.

Synthesis of α-Z-ε-3-butenoyl-L-lysine-OH

α-Z-L-lysine (2.5 g, 9.0 mmol) and NaHCO$_3$ (0.8 g, 9.9 mmol) were dissolved in a THF/water mixture (25 mL/25 mL). The alkene NHS-ester (1.9 g, 6.8 mmol) prepared as above was dissolved in THF and then added to the mixture containing α-Z-L-lysine. The reaction proceeded at room temperature overnight. THF was then removed under vacuum. HCl (1 N) was added to adjust its pH to ~3.50 mL of ethylacetate was added to the solution and transferred to a 250-mL separatory funnel. The organic and aqueous phases were separated and individually collected. The product was in the organic phase containing ethylacetate. Fresh ethylacetate was added to the aqueous phase and the separation and collection procedure was repeated for another few times. All of the ethylacetate solutions containing the product were combined together and filtered through a glass filter. The filtrate was then collected. Most of the ethylacetate was removed by rotorvap and then extensively dried under vacuum. We tried to re-crystallize the product by using the solvent pair of ethylacetate/hexane (10 mL/50 mL) at −20° C. for one month. Some white powder appeared over time. The solvent was removed under vacuum and thy white powder was obtained (2.9 g). Further investigation into an appropriate solvent combination is expected to allow for the successful re-crystallization subsequently. $^1$H-NMR (500 MHz, CDCl$_3$, δ ppm): 1.25, 1.55, 1.78, 2.85, 3.02, 4.55, 5.09, 5.21, 5.24, 5.94, 7.38, 7.47, 8.03.

Alkene-Functionalized Polymer 5, 10, and 20 equiv. of 3-butenoic acid per lysine residue were individually conjugated to the N$_\epsilon$-amines of poly-L-lysine in K$_{180}$L$_{20}$ via amine coupling with NHS and EDC at pH 7.8 in bicarbonate buffer. The reactions proceeded for 2 days and the mixtures were then acidified to ensure the residual N$_\epsilon$-amines were protonated. The mixtures were then transferred to dialysis bags (Regenerated Cellulose, Spectra/Por, MWCO 6-8 kDa) that were placed in sterile 4-L containers of pyrogen free water. The water was replaced twice a day for 5 days. The solutions were then freeze-dried to yield the products as spongy solids. Conjugation K$_{180}$L$_{20}$ with 10 and 20 equiv. of 3-butenoic acid was not soluble in water after dialysis and Lyophilization. Only the K$_{180}$L$_{20}$ samples conjugated with 5 equiv. of 3-butenoic acid was able to form a hydrogel in water at the concentration of 3%. In order to confirm the successful conjugation of the alkene groups to K$_{180}$L$_{20}$, both carbon and proton NMR spectra were taken. However, due to the low number of alkene groups conjugated per K$_{180}$L$_{20}$ chains and the diminished solubility of the polymer in the deuterated solvents (d-TFA, D$_2$O, or d-TFA/D$_2$O mixtures), the quality of the NMR spectra were poor. Samples in better solvents, or in the solid state, are required to obtain good NMR spectra. In proton NMR spectra, we could observe resonances of the protons from lysine and leucine residues, but not from the alkene groups. The percentage of alkene groups per lysine residue is ~3%, which also makes detection difficult. In order to attach more alkene groups and still preserve the aqueous solubility of the polymer, K$_{200}$ will be used for future model conjugation studies.

4. In vivo injections of DCH were carried out as discussed above.

In this Example, the injection was only performed on one side. The dose of either chABC (Seikagaku Corp., East Falmouth, Mass., USA) or control bacteria enzyme (penicillinase, Sigma, St. Louis, Mo., USA) in physiological saline was 50 U/mL.

5. Histological procedures were carried out as discussed above.

Primary antibodies were: monoclonal mouse anti-2B6 (1:3,000; Seikagaku); Bio-WFA (1:2,500; Sigma-Aldrich).

D. Results and Discussion

1. Covalent Binding a. Loss of Activity of Proteins after Lyophilization

Bioconjugation work was performed with horseradish peroxidase (HRP), ovalbumin, and laminin-1. These proteins were conjugated (at the ratio ranging from 1 to 0.01 proteins per polymer chain) to K$_{180}$L$_{20}$ via amine coupling. The polymers were then freeze-dried after dialysis. Upon rehydration, some loss in protein activity was observed. Since freeze-drying (lyophilization) removes water from a frozen sample by sublimation and desorption, this could cause structural changes in the conjugated proteins and the gel network. Routine optimization of freeze drying of proteins conjugated to DCH will be carried out in order to improve the ability to store these sample as lyophilized powders.

b. Alkene-functionalization; Synthesis of α-CBZ-ε-Vinyl-L-lysine-OH

Proton NMR showed that α-CBZ-ε-Vinyl-L-lysine-OH was synthesized. In order to proceed to the next step to synthesize the NCA monomer, a better purification approach will be carried out to obtain the compound with high purity.

2. DCHs Preserve the Bioactivity of chABC

Figure 10:
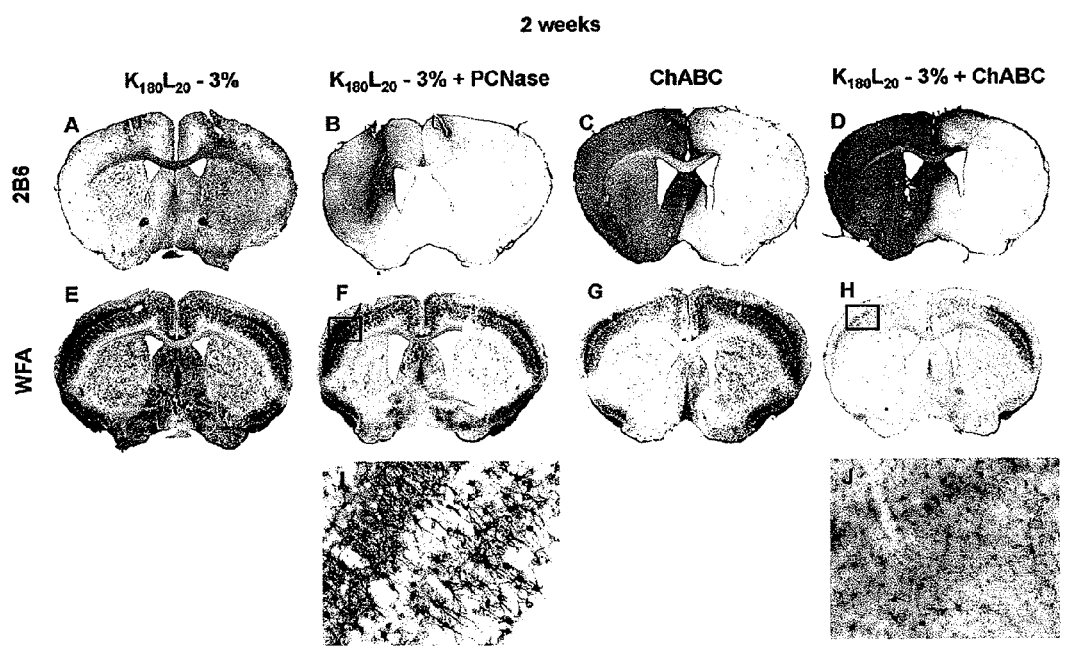
FIG. 10 shows WFA and 2B6 stained tissue sections injected with 3% -$K_{180}L_{20}$ with or without penicillinase or chABC into the CPN on the left side of the forebrain after 2 weeks in vivo.

ChABC belongs to a family of bacterial enzymes which cleave glycosaminoglycan (GAG) chains by a β-elimination mechanism. This enzyme, as its name suggests, digests chondroitin sulfate (CS)-A, -B and -C isoforms which correspond to chondroitin 4-sulfate (C4S), dermatan sulfate (DS) and chondroitin 6-sulfate (C6S) respectively (Yamagata et al. (1968) Purification and properties of bacterial chondroitinases and chondrosulfatases, *J Biol Chem* 243, 1523-1535). The intact CSPGs could be recognized by the N-acetylgalactosamine-binding *Wisteria floribunda* agglutinin (WFA) antibody, and the "stubs" on C4S core proteins remaining after digestion of CSPGs by chABC sould be recognized by the 2B6 antibody. When the CSPGs were digested, tissue sections were less stained by WFA immunohistochemistry (the left side of forebrain sections in FIG. 10G, H, J), and exhibited greater staining by 2B6 immunohistochemistry (the left side of the forebrain sections in FIG. 10C, D). Both control groups, 3%-K$_{180}$L$_{20}$ alone and mixed with penicillinase (a non-active control protein), showed no digestive activity on CSPGs in vivo (FIG. 10A, B, E, F, I).

Figure 11:
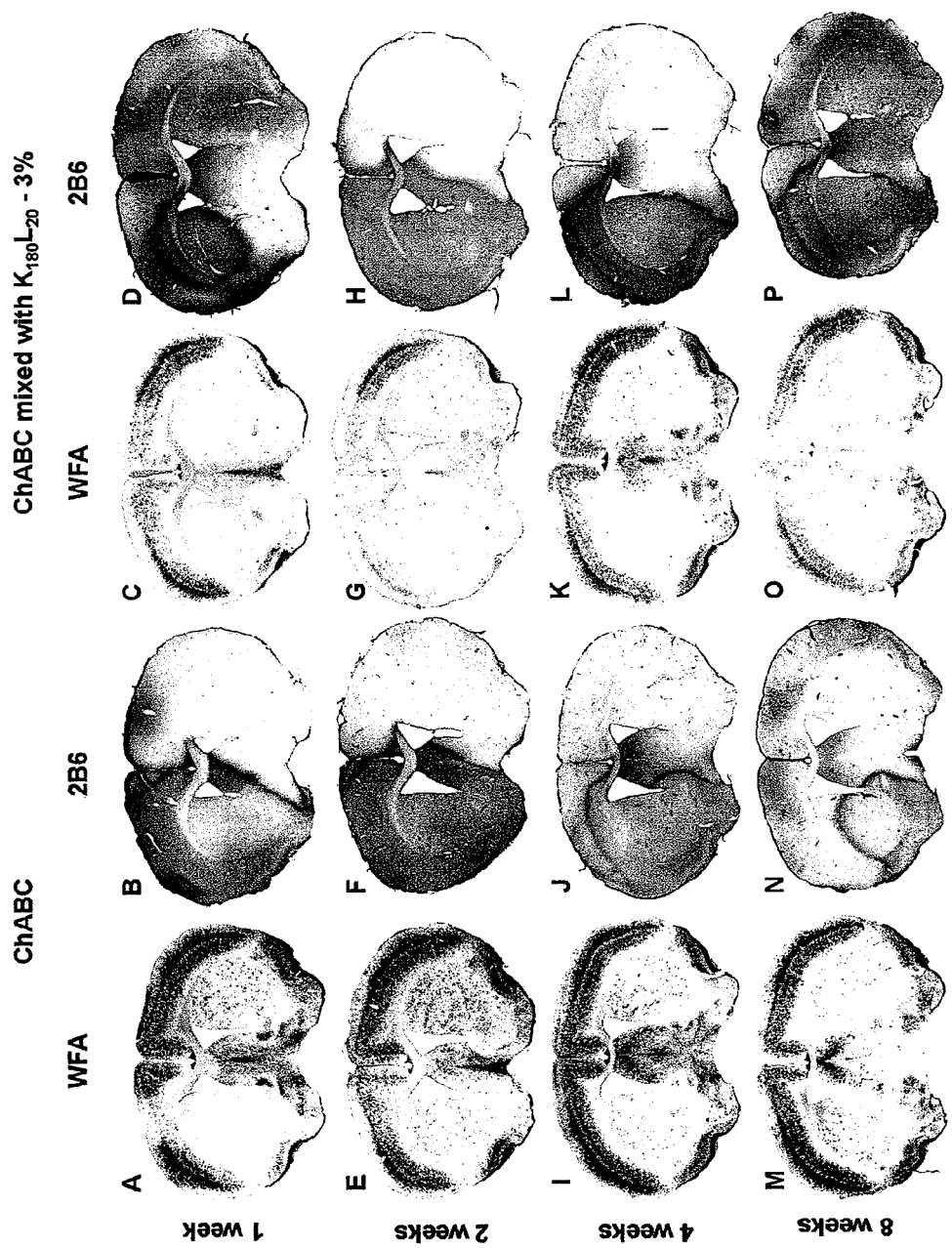
FIG. 11 shows in vivo bioactivity of chABC alone or mixed with 3%-$K_{180}L_{20}$ after 1-8 weeks.

We compared the in vivo bioactivity of chABC dissolved in saline (FIG. 11A, B, E, F, I, J, M, N), or mixed with 3%-K$_{180}$L$_{20}$ (FIG. 11C, D, G, H, K, L, O, P), or conjugated to 3%-K$_{180}$L$_{20}$ (data not shown) 3%-K$_{180}$L$_{20}$ from 1 to 8 weeks. Our findings indicate that the in vivo bioactivity of chABC dissolved in saline lasted from 2 to 4 weeks (FIG. 11E, F, I, J). When chABC was mixed with DCH, its bioactivity appeared to last from 4 to 8 weeks (FIG. 11K, L, O, P). Overall, we found that bioactive chABC could be released from the 3%-K$_{180}$L$_{20}$ hydrogel, and its overall in vivo digestive capability on CSPGs was prolonged by mixing in DCH.

Although TEC is a century-old reaction, in order to apply it to bioconjugation, it has to be easily carried out in an aqueous environment at physiological pH and low temperature (about 4° C. to room temperature) in a reasonable reaction time period. However, such reaction conditions for the bioconjugation had not been developed prior to the present application. We show here some methods which use suitable reaction conditions.

We also found that bioactive chABC could be released from DCH deposits, and its overall in vivo digestive capability on CSPGs was prolonged by entrapment in DCH.

Example III

Biocompatibility of Amphiphilic Diblock Copolypeptide Hydrogels in the Central Nervous System/Use as Scaffolds A. Introduction There is a tremendous demand for tissue engineered organs. The number of people on the waiting list for organ transplantation surpasses the number of organs donated, and this situation is predicted to get even more serious as the population ages. Engineered skin and cartilage have recently been introduced for clinical use. Several other potential tissue types for substitutive treatment are currently under investigation, including liver, bone, muscle, adipose, and nervous tissues. However, the engineering of more complex tissues consisting of large 3D structures remains a critical challenge. Because the amount of oxygen required for cell survival is limited to a diffusion distance of approximately 150 to 250 µm from the supplying blood vessel, long-term survival and function of such 3-dimensionally constructed tissues depends on rapid development of new blood vessels, which provide nutrients and oxygen to the cells not only at the boundaries but also in the center of the tissue grafts. In fact, the growth of a new microvascular system remains one of the major limitations in the successful introduction of tissue engineering products to clinical practice.

Angiogenesis refers to the formation of new capillary blood vessels by a process of sprouting from pre-existing vessels or precursor cells of endothelia that participate in embryogenesis as well as normal and pathological vessel formation in postnatal life. The process of angiogenesis is orchestrated by endothelial cells and neighboring mural cell types via various growth factors and extracellular matrix proteins. There have been numerous reports on design and optimization of scaffold materials to promote local angiogenesis directly in vivo and to encourage infiltration of host vessels into the scaffolds. Even for scaffolds pre-vascularized ex vivo, successful integration of the implant with the host tissues largely depends on vessel and cellular in-growth.

We demonstrated previously that the deposits of 3%-$K_{180}L_{20}$ were densely vascularized with well-formed blood vessels and normally appearing endothelia by 4 weeks after injection in vivo. By 8 weeks in vivo, the deposits exhibited a cell density approximately similar to that of neighboring host tissue and contained three different types of host glia cells. This suggests the potential for DCH deposits to serve as scaffolds for cell migration in the CNS if they are functionalized with the appropriate migration guidance cues. The large glycoprotein laminin-1 (800-kD) is a major ECM protein (Martin et al. (1987) Laminin and other basement membrane components, *Annu Rev Cell Biol* 3, 57-85) that promotes cell attachment, tumor metastasis, and angiogenesis (Malinda et al. (1999) Identification of laminin alpha1 and beta1 chain peptides active for endothelial cell adhesion, tube formation, and aortic sprouting, *FASEB J* 13, 53-62; Kibbey et al. (1995) A 110-kD nuclear shuttling protein, nucleolin, binds to the neurite-promoting IKVAV (SEQ ID NO:1) site of laminin-1, *J Neurosci Res* 42, 314-322). The ile-lys-val-ala-val (IKVAV)-containing site on the long arm of the laminin al chain (Tashiro et al. (1989) A synthetic peptide containing the (SEQ ID NO:1) IKVAV sequence from the A chain of laminin mediates cell attachment, migration, and neurite outgrowth, *J Biol Chem* 264, 16174-16182) has also been reported to promote cell adhesion, neurite outgrowth, and angiogenesis (Tashiro et al. (1989) (supra); Sephel et al. (1989) Laminin A chain synthetic peptide which supports neurite outgrowth, *Biochem Biophys Res Commun* 162, 821-829; Grant et al. (1992) Interaction of endothelial cells with a laminin A chain peptide (SIKVAV) (SEQ ID NO:3) in vitro and induction of angiogenic behavior in vivo, *J Cell Physiol* 153, 614-625; Dixelius et al. (2004) Laminin-1 promotes angiogenesis in synergy with fibroblast growth factor by distinct regulation of the gene and protein expression profile in endothelial cells, *J Biol Chem* 279, 23766-23772). Laminin-1 and IKVAV (SEQ ID NO:1) were each incorporated into DCHs to enhance functionality and test the feasibility of DCHs as scaffolds in the CNS.

B. Methods

1. Synthesis of DCH was performed as discussed above.
2. Laminin or IKVAV (SEQ ID NO:1) were conjugated to DCH as discussed above.

Laminin-1 (R&D Systems, Minneapolis, Minn., USA) or (SEQ ID NO:1) IKVAV (American Peptide, Sunnyvale, Calif., USA) was conjugated to $K_{180}L_{20}$ via amide bond coupling. The final concentration of laminin was 0.5 mg/mL. The conjugation ratio of (SEQ ID NO:1) IKVAV was 5 molecules per $K_{180}L_{20}$ polymer chain.

3. In vivo injections of DCH was performed as discussed above.

In this study, samples of unmodified or IKVAV (SEQ ID NO:1)-conjugated $K_{180}L_{20}$ were injected into both sides of the forebrain. Laminin decorated 3%-$K_{180}L_{20}$ were injected into one side of the forebrain only.

4. Histological procedures were performed as discussed above.

C. Results

1. Cell Migration and Angiogenesis in Laminin-1 Decorated DCH Deposits

Figure 12:
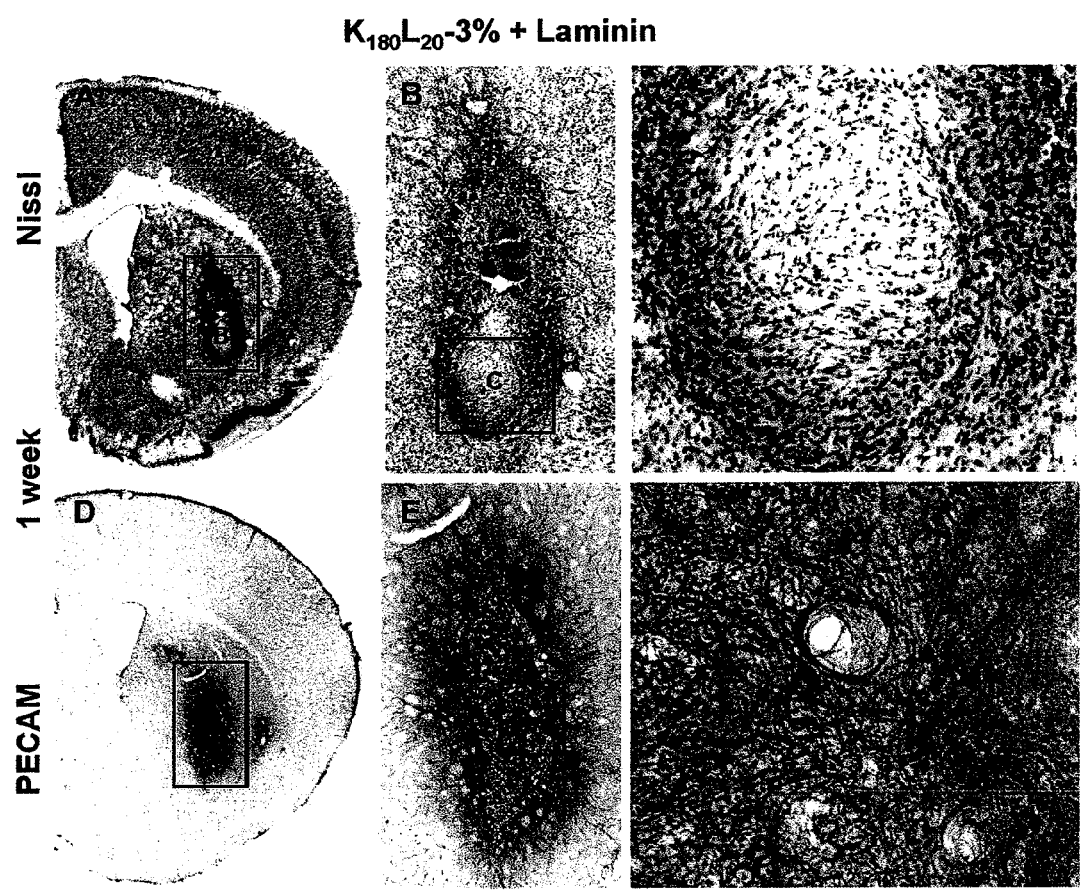
FIG. 12 shows that laminin decorated 3%-$K_{180}L_{20}$ promoted cell in-migration and angiogenesis after 1 week in vivo. (A-F) show survey (A, D), intermediate (boxes B, E), and detail (boxes C, F) images of cresyl violate stained tissue sections (A-C) and the tissue sections immunohistochemically stained for the endothelial cell marker, PECAM (D-F), through the CPN. Note that the deposits are densely packed with cells after 1 week in vivo (A-C). DCH deposits with laminin were well vascularized and contained many well-formed blood vessels with normally appearing endothelial cells throughout the deposits after 1 week in vivo (D-F).

In contrast to unmodified DCH, after 1 week in vivo, the laminin modified gel deposits were densely packed with cells (FIG. 12A-C). Deposits of laminin-1 decorated 3%-$K_{180}L_{20}$ DCH deposits were well vascularized and contained many well-formed blood vessels with normally appearing endothelial cells throughout the deposits after 1 week in vivo (FIG. 12D-F).

Laminin-1 decorated 3%-$K_{180}L_{20}$ significantly promoted cell in-migration and angiogenesis in the forebrain at 1 week after injection. These results are comparable to the previously demonstrated in-migration of cells and angiogenesis of unmodified 3%-$K_{180}L_{20}$ after 4 weeks in vivo.

Figure 13:
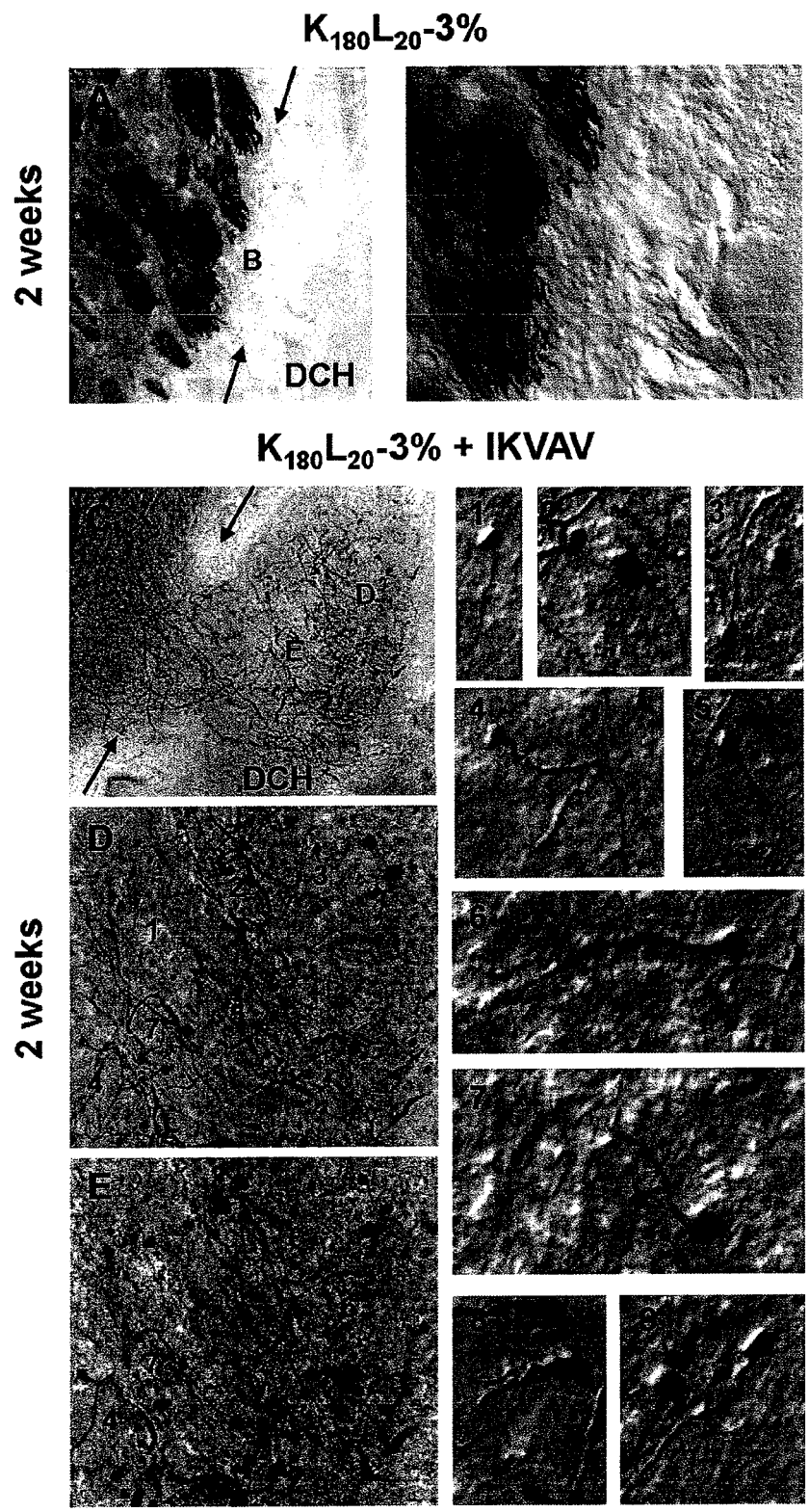
FIG. 13 shows that forebrain deposits of DCH decorated with IKVAV (SEQ ID NO:1) exhibit in-growth of NFM-positive nerve fibers. (A-E) Survey and detail images show tissue sections through the mouse forebrain immunohistochemically stained for neurofilament M to identify nerve fibers at two weeks after injection of DCH without (SEQ ID NO:1) IKVAV (A, B) or DCH with (SEQ ID NO:1) IKVAV (C-E). No nerve fibers grew from surrounding tissue into DCH deposits without (SEQ ID NO:1) IKVAV (A,B). Nerve fibers did grow from surrounding tissue into deposits of DCH decorated with (SEQ ID NO:1) IKVAV (C-E). (C) shows a survey image of a DCH deposit with IKVAV (SEQ ID NO:1). Note the many long fibers traversing from the host tissue on the left into the deposit on the right. Arrows delineate the border of the DCH deposit. (D, E) show at higher magnification the nerve fibers growing in the center of the deposit (areas labeled D and E in C). Note that there are many nerve fibers with round growth cones grow randomly in many directions. Numbers indicate individual nerve fibers with growth cones shown at higher magnification on the right.
Figure 14:
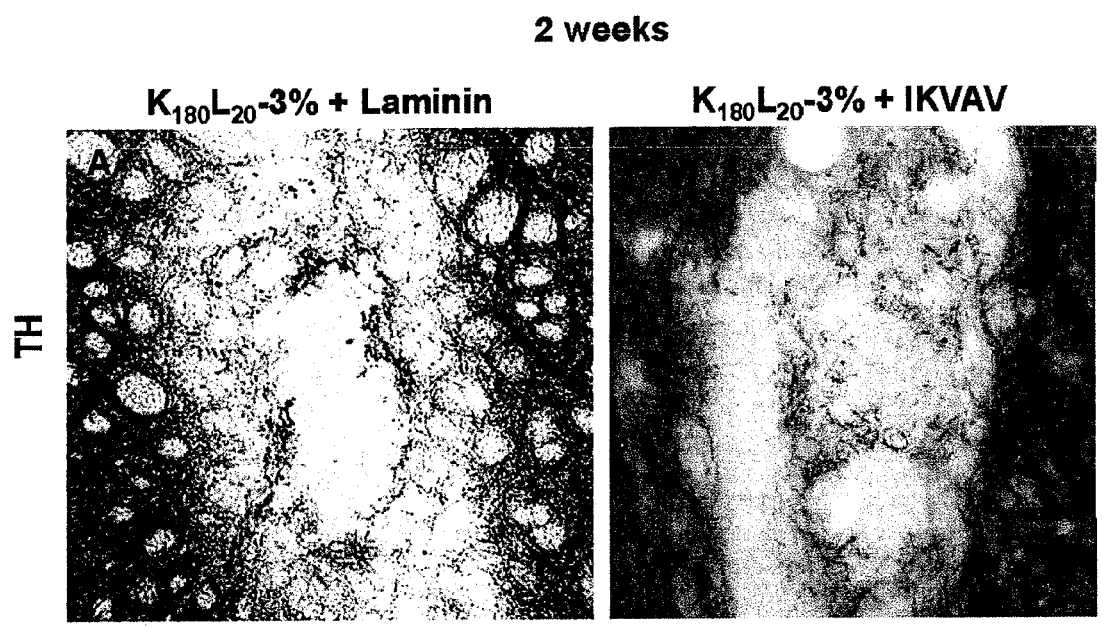
FIG. 14 shows that forebrain deposits of DCH decorated with laminin or (SEQ ID NO:1) IKVAV exhibit in-growth of TH-positive nerve fibers. (A, B) Images of tissue sections through the CPN immunohistochemically stained for the nerve fiber markers, TH, at 2 weeks after injection of 3% $K_{180}L_{20}$ SEQ ID NO:8) with laminin (A) or (SEQ ID NO:1) IKVAV (B). Nerve fibers grew from surrounding tissue into deposits of DCH decorated with laminin (A) or (SEQ ID NO:1) IKVAV (B). Note the normal appearance of and high density of TH-positive axons in the host CPN immediately adjacent to and into the center of DCH deposits (A, B).

Nerve Fiber In-growth into Laminin-1 or IKVAV (SEQ ID NO:1) Decorated DCH Deposits As described above, at 2 weeks after injection, deposits of unmodified 3%-$K_{180}L_{20}$ exhibited no appreciable in-growth of nerve fibers positive for either NFM or TH. After 4 or 8 weeks in vivo, small numbers of single NFM-positive fibers were found crossing from the host into the deposits along the borders, and occasional NFM fibers were found within the center of deposits, generally in association with blood vessel walls. After 4 or 8 weeks in vivo, somewhat larger numbers of TH-positive fibers, often as bundles of fibers, were found crossing from the host into the deposits, particularly along the borders and sometimes penetrating well into the center of deposits, sometimes, but not always, in association with blood vessel walls. After 2 weeks in vivo, deposits of IKVAV (SEQ ID NO:1) conjugated 3%-$K_{180}L_{20}$ exhibited many NFM-positive nerve fibers with round growth cones growing randomly in many directions (FIG. 13). At 2 weeks after injection, many TH-positive axons with normal appearance were found in the deposits of IKVAV (SEQ ID NO:1) conjugated or laminin-1 decorated 3%-$K_{180}L_{20}$.

These studies indicate that laminin-1 decorated 3%-$K_{180}L_{20}$ significantly promotes cell in-migration and angiogenesis after 1 week in vivo. Both IKVAV (SEQ ID NO:1) and laminin-1 decorated 3%-$K_{180}L_{20}$ exhibited appreciable in-growth of nerve fibers.

Example IV

Loading of DCH with Bioactive Proteins and Release of these Cargos in vivo

Providing sustained local, site-restricted release of diffusible bioactive molecules, such as polypeptide growth factors, function blocking hybrid proteins, oligonucleotides and certain enzymes are applications well-suited to injectable biomaterial depots such as DCH. This study examined (a) the release kinetics of bioactive molecules from DCH depots in vitro and (b) the efficacy of molecular delivery from DCH depots in vivo. In addition, the uptake of polypeptide nanocarriers plus oligonucleotides into CNS cells in vivo was evaluated.

We have shown that DCH depots will release molecules into the surrounding host CNS tissue and that the release rate can be varied and controlled in various ways, either by using cleavable linkers to bind molecules to the DCH or by loading molecules into vesicles or emulsions. Different kinds of molecules require different delivery methods, and optimizing delivery can be accomplished with a combination of routine, conventional informed design and empirical testing.

This Example demonstrates sustained extracellular delivery release of different proteins such as enzymes, function blocking hybrid molecules and growth factors. Delivery of proteins was evaluated by comparing release from DCH depots under three different conditions: (i) dissolved in DCH; (ii) bound to DCH by permanent linker; and (iii) bound to the DCH by a reversible linker. Release kinetics associated with these three conditions was evaluated in vitro by measuring the escape of fluorescence-tagged proteins (Texas Red labeled BSA) from DCH across a border of dialysis tubing porous to the proteins but not to DCH. Dialysis tubing porous to the tags but not the proteins was used as control. Release in vivo was characterized after injection of different DCH formulations into the mouse forebrain as done previously. Different DCH formulations were injected into the forebrain and release of bioactive molecules in vivo was determined by analysis of bioactivity or direct protein assay by ELISA.

Figure 15:
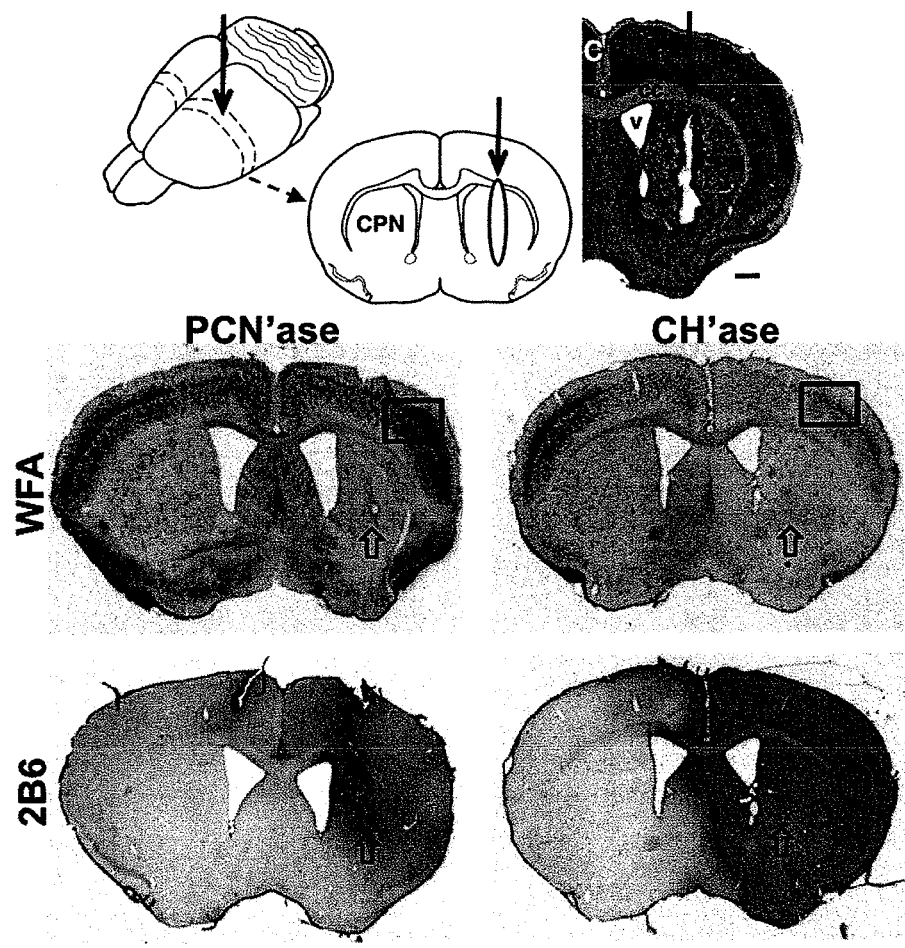
FIG. 15 shows the delivery of bioactive chondroitinase by DCH deposits in vivo. Images show degradation of CSPGs resulting in loss of WFA staining and exposure of 2B6 antigen, 2 weeks after forebrain injection of DCH+chondroitinase (CH'ase). Delivery of the control enzyme, penicillinase (PCH'ase), does not have these effects.

Chondroitinase is an enzyme that degrades the axon growth inhibitors, chondroitin sulfate proteoglycans (CSPG). Release of bioactive chondroitinase from DCH depots in vivo is demonstrated in FIG. 15. DCH depots can effectively deliver bioactive proteins dissolved in the DCH; and bioactive molecules gradually escape from DCH into surrounding host tissue and exert effects with full potency.

Example V

Loading of DCH with Nanocarriers (Vesicles and Emulsions) to Release or Promote Cellular Uptake of Encapsulated or Entrapped Cargos in vivo Some bioactive molecules with therapeutic potential for the CNS require encapsulation to prevent their degradation and need to be delivered intracellularly (e.g. siRNA and plasmids). We have developed materials and strategies for loading of encapsulated bioactive molecules into DCH to achieve their sustained release over variable times at restricted sites after injections of DCH deposits in vivo.

We demonstrate in this Example the successful loading of vesicle and emulsion nanocarriers into DCH and their release and subsequent intracellular uptake in the CNS. Our previous work on intracellular delivery using polypeptide vesicles and emulsions, including double emulsion droplets, and their dispersion in DCH (see, e.g, Holowka et al. (2007), "Polyarginine segments in block copolypeptides drive both vesicular assembly and intracellular delivery" *Nature Materials* 6, 52-57) provided us with the expertise to successfully entrap molecules using these carriers within DCH to obtain useful biological effects.

Figure 16:
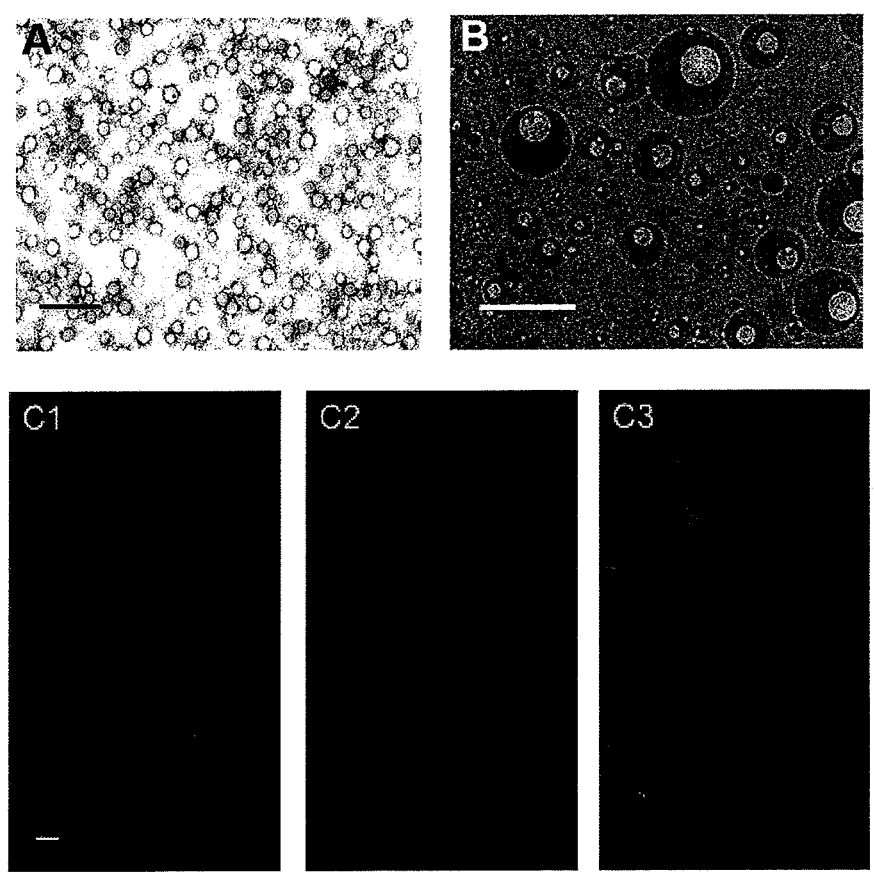
FIG. 16 shows polypeptide vesicle and double emulsion nanocarriers in DCH.

We previously prepared block copolypeptides ($K_{60}L_{20}$) that assemble into stable vesicles in aqueous solution, can be sized to 100 nm diameter, and are able to entrap and deliver polar siRNA molecules to cells in culture. See, e.g., US patent publication 2010/0003336. We have also prepared similar copolypeptides ($K_{40}$(racemic-L)$_{20}$) that emulsify oil and water mixtures to yield nanoscale (10 s to 100 s of nm diameter) double emulsion droplets that efficiently entrap both hydrophilic and hydrophobic cargos. See, e.g, Hanson et al. (2008) "Nanoscale Double Emulsions Stabilized by Single Component Block Copolypeptides" *Nature* 455, 85-89. These were found in the present experiment to be taken up by neurons after injection into the CNS (FIG. 16). The cationic peptidic nature of these nanocarriers makes them highly compatible with the DCH of the present invention, e.g. $K_{180}L_{20}$, allowing their mixture without disruption of either assembly. We have formed complexes of oligonucleotides separately with vesicle and double emulsion nanocarriers by mixing solutions of each to allow electrostatic binding, followed by extrusion through different polycarbonate nucleopore filters to control carrier size and enhance entrapment of siRNA. These complexes were loaded into DCH by dissolution of $K_{180}L_{20}$ powder into the nanocarrier suspension. Release of nanocarriers from DCH depots into CNS cells in vivo (FIG. 16) was demonstrated. Development of biomaterial depots and scaffolds that contain regularly dispersed nanocarriers, which can controllably diffuse from the scaffold, with the ability to deliver bioactive molecules is an advantage for controlled intracellular delivery to the CNS. This work provides well-characterized materials for both in vitro and in vivo studies on release and cellular uptake of molecules from DCH, and also validates a new dual material, nanocarrier in scaffold strategy for therapeutic delivery.

From the foregoing description, one skilled in the art can easily ascertain the essential characteristics of this invention, and without departing from the spirit and scope thereof, can make changes and modifications of the invention to adapt it to various usage and conditions and to utilize the present invention to its fullest extent. The preceding preferred specific embodiments are to be construed as merely illustrative, and not limiting of the scope of the invention in any way whatsoever. The entire disclosure of all applications, patents, and publications cited above (including provisional application 61/153,527, filed Feb. 18, 2009; and U.S. provisional application 61/186,671, filed Jun. 12, 2009) are hereby incorporated by reference in their entireties.

We claim:

1. A composition suitable for administration to the central nervous system (CNS), comprising a block copolypeptide hydrogel, wherein the block copolypeptide comprises a hydrophobic domain comprising poly-L-leucine (L) and a hydrophilic domain comprising racemic poly-D/L-lysine (rac-K) or poly-L-lysine (K), wherein the block copolypeptide comprises between about 200 and 600 amino acids, wherein the composition comprises chondroitinase ABC (chABC), that is mixed with the hydrogel and/or is attached to the polypeptide backbone of the hydrogel.

2. The composition of claim 1, wherein the block copolypeptide is a diblock copolypeptide.

3. The composition of claim 1, wherein chABC is entrapped in a nanocarrier, which is mixed with the hydrogel.

4. The composition of claim 3, wherein the nanocarrier is a vesicle or a double emulsion droplet.

5. The composition of claim 1, wherein chABC is covalently attached to the polypeptide backbone of the hydrogel.

6. The composition of claim 5, wherein chABC enhances axonal plasticity and/or improves functional recovery after peripheral nerve repair following spinal cord injury.

7. The composition of claim 1, wherein the chABC is covalently attached to the polypeptide backbone, and the covalent attachment is achieved by thiol-ene coupling (TEC) of a thiol group of chABC which has been thiolated to an alkene-functionalized group of the polypeptide backbone.

8. The composition of claim 1, wherein the block copolypeptide consists essentially of $K_{180}L_{20}$ (SEQ ID NO:8).

9. A method for making the composition of claim 1, comprising covalently attaching chABC to the polypeptide backbone, by
  a) thiolating chABC,
  alkene-functionalizing a group of the polypeptide backbone, and thiol-ene coupling (TEC) a thiolated group of chABC to an alkene-functionalized group of the polypeptide backbone, or
  b) thiolating a group of the polypeptide backbone,
  alkene-functionalizing chABC, and thiol-ene coupling (TEC) a thiolated group of the polypeptide backbone to an alkene-functionalized group of chABC.

10. The method of claim 9, wherein the TEC is carried out in an aqueous solution at physiological pH and at about 4° C.-room temperature.

11. A method for making a composition of claim 1, comprising covalently attaching chABC to the polypeptide backbone by amine coupling.

12. A method for introducing biologically active chABC into a brain in vivo, comprising injecting a composition of claim 1 into the brain.

13. A method for providing a scaffold for enhancing axonal plasticity and/or improving functional recovery after peripheral nerve repair following spinal cord injury in the central nervous system (CNS), comprising functionalizing a block copolypepide hydrogel of claim 1 with chABC.

14. A method for stimulating the in-growth of nerve fibers, in a brain, comprising introducing into the brain a scaffold of claim 6.

15. The method of claim 14, which enhances axonal plasticity and/or improves functional recovery after peripheral nerve repair following spinal cord injury.

16. A kit comprising
  (a) a block copolypeptide of claim 1, which has been lyophilized, and an aqueous solution comprising chABC, with which the lyophilized block copolypeptide can be reconstituted; or
  (b) a block copolypeptide of claim 1, which been chemically functionalized with chABC, and which has been lyophilized, and, optionally, an aqueous solution with which the functionalized, lyophilized block copolypeptide can be reconstituted.

* * * * *